US007238269B2

(12) United States Patent
Gason et al.

(10) Patent No.: US 7,238,269 B2
(45) Date of Patent: Jul. 3, 2007

(54) SAMPLE PROCESSING DEVICE WITH UNVENTED CHANNEL

(75) Inventors: Samuel J. Gason, St. Paul, MN (US); William Bedingham, Woodbury, MN (US); Bathsheba E. Chong Conklin, St. Paul, MN (US); Patrick L. Coleman, Minneapolis, MN (US); Peter D. Ludowise, Cottage Grove, MN (US); Isidro Angelo E. Zarraga, Minneapolis, MN (US)

(73) Assignee: 3M Innovative Properties Company, St. Paul, MN (US)

(*) Notice: Subject to any disclaimer, the term of this patent is extended or adjusted under 35 U.S.C. 154(b) by 665 days.

(21) Appl. No.: 10/610,949

(22) Filed: Jul. 1, 2003

(65) Prior Publication Data

US 2005/0199500 A1 Sep. 15, 2005

(51) Int. Cl.
*G01N 27/447* (2006.01)
*G01N 27/453* (2006.01)
*C12Q 1/68* (2006.01)
*B01L 3/00* (2006.01)

(52) U.S. Cl. ...................... 204/459; 204/610; 204/451; 204/601; 422/50; 422/99

(58) Field of Classification Search ................ 204/450, 204/451, 600, 601, 610, 459; 422/99, 100, 422/70, 50
See application file for complete search history.

(56) References Cited

U.S. PATENT DOCUMENTS 4,708,782 A 11/1987 Andresen et al.
5,126,022 A 6/1992 Soane et al.
5,160,702 A * 11/1992 Kopf-Sill et al. ............. 422/72
5,750,015 A 5/1998 Soane et al.
6,017,765 A 1/2000 Yamada et al.
6,068,751 A 5/2000 Neukermans
6,143,152 A 11/2000 Simpson et al.
6,284,113 B1 9/2001 Bjornson et al.
6,302,134 B1 10/2001 Kellogg et al.
6,303,343 B1 10/2001 Kopf-Sill
6,306,273 B1 10/2001 Wainright et al.
6,319,469 B1 11/2001 Mian et al.
6,532,997 B1 3/2003 Bedingham et al.
6,610,186 B1 * 8/2003 Mayer et al. ............... 204/451
6,662,830 B2 * 12/2003 Bedingham et al. .......... 141/34
6,734,401 B2 5/2004 Bedingham et al.

(Continued)

FOREIGN PATENT DOCUMENTS

JP 08233778 A * 8/1996

(Continued)

OTHER PUBLICATIONS

Definition of "hub" in Merriam-Webster's Collegiate Dictionary, 10th edition, 1998.*

(Continued)

*Primary Examiner*—Alex Noguerola
(74) *Attorney, Agent, or Firm*—Sean J. Edman

(57) ABSTRACT

A device includes a substrate having first and second major surfaces and a hub that defines an axis of rotation for the substrate, and an unvented channel having a plurality of connected compartments. Methods for using devices of the invention are also disclosed.

42 Claims, 27 Drawing Sheets

U.S. PATENT DOCUMENTS

| | | | | |
|---|---|---|---|---|
| 6,766,817 | B2 | 7/2004 | da Silva | |
| 6,814,935 | B2 | 11/2004 | Harms et al. | |
| 6,987,253 | B2 * | 1/2006 | Bedingham et al. | 219/752 |
| 2002/0047003 | A1 | 4/2002 | Bedingham et al. | |
| 2002/0048533 | A1 | 4/2002 | Harms et al. | |
| 2002/0064885 | A1 | 5/2002 | Bedingham et al. | |
| 2002/0155591 | A1 | 10/2002 | Farina et al. | |
| 2003/0118804 | A1 | 6/2003 | Bedingham et al. | |
| 2003/0120062 | A1 | 6/2003 | Parthasarathy et al. | |
| 2003/0138779 | A1 | 7/2003 | Parthasarathy et al. | |
| 2004/0137634 | A1 | 7/2004 | Robole et al. | |

FOREIGN PATENT DOCUMENTS

| | | | |
|---|---|---|---|
| WO | WO 98/22625 | A1 | 5/1998 |
| WO | WO 00/17624 | A2 | 3/2000 |
| WO | WO 00/45180 | A1 | 8/2000 |
| WO | WO 00/62931 | A1 | 10/2000 |
| WO | WO 00/68336 | A1 | 11/2000 |
| WO | WO 01/02737 | A1 | 1/2001 |
| WO | WO 01/25137 | A1 | 4/2001 |
| WO | WO 01/25138 | A1 | 4/2001 |
| WO | WO 01/27253 | A1 | 4/2001 |
| WO | WO 01/30995 | A1 | 5/2001 |
| WO | WO 01/31322 | A1 | 5/2001 |
| WO | WO 01/47637 | A1 | 7/2001 |
| WO | WO 01/47638 | A2 | 7/2001 |
| WO | WO 01/54810 | A1 | 8/2001 |
| WO | WO 01/067087 | | 9/2001 |
| WO | WO 01/86249 | A2 | 11/2001 |
| WO | WO 02/00347 | | 1/2002 |

OTHER PUBLICATIONS

JPO English language computer translation of Arai (JP 08233778 A).*

Nist Grant, Project Brief [online], "Tools for DNA Diagnostic (Oct. 1998) Integrated, Micro-Sample Preparation System for Genetic Analysis," [retrived on Aug. 5, 2002] 2 pgs. Retrieved from the internet at <http://jazz.nist.gov/atpcf/prjbriefs/prjbrief.cfm?ProjectNumber=98-08-0031>.

Scherer et al., "High-Pressure Gel Loader for Capillary Array Electrophoresis Microchannel Plates," *Biotechniques*; vol. 31; No. 5; pp. 1150-1154 (Nov. 2001).

U.S. Appl. No. 10/339,447, "Sample Processing Device Having Process Chambers With Bypass Slots", Robole et al., filed Jan. 9, 2003.

* cited by examiner

SAMPLE PROCESSING DEVICE WITH UNVENTED CHANNEL

FIELD OF THE INVENTION

The invention relates to a device useful for separation and/or fractionation of analyte samples.

BACKGROUND OF THE INVENTION

Two-dimensional separation systems for protein samples are of great interest because of their increased peak capacity over one-dimensional systems. For example, separation of a complex protein mixture is currently performed using two-dimensional poly(acrylamide) gel electrophoresis, in which proteins are first separated by their iso-electric points, and then by size. The technique gives excellent separation of the protein mixture, but is very time consuming and labor intensive. Furthermore, because the proteins are embedded in the gel matrix, extensive protocols involving destaining, in-gel digestion, and extraction are necessary for further analysis by mass spectrometry, for example. Procedures that require considerable human intervention and a number of fluid transfers such as these can result in errors, contamination, and exposure to potential biohazards. Therefore, there remains a need for a device that is capable of providing limited user-intervention for two-dimensional separation and subsequent analysis.

SUMMARY OF THE INVENTION

The invention provides a device that includes a substrate having first and second major surfaces and a hub defining an axis of rotation for the substrate, and an unvented channel adapted to fractionate a sample. In one embodiment, the unvented channel includes a plurality of connected compartments. In another embodiment, the device also includes at least one integrated electrode, which can be releasably attached to or integrated into the substrate of the device.

The invention also provides devices that further include connection structures and other features that are at least connected to the unvented channel through the connection structures.

The invention also provides methods for using devices in accordance with the invention. For example, the devices of the invention are useful for performing processing, separation and/or fractionation of analyte samples. Accordingly, the devices may, in some embodiments, be adapted for carrying out isoelectric focusing and/or capillary electrophoresis.

Other advantages and features of the present invention will be apparent from the following detailed description, the drawings, and the claims.

DETAILED DESCRIPTION OF THE INVENTION

The invention provides devices that include a substrate and an unvented channel. In one embodiment of the invention, the device can be used for sample processing. For example, the device can be utilized to run electrophoretic separation, including iso-electric focusing on a sample.

Device of the Invention

Figure 1A:
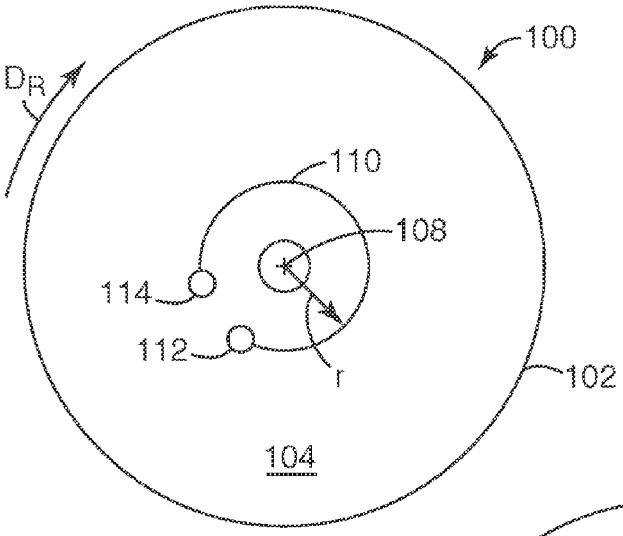
FIGS. 1*a, b, c, d*, and *e* are plan views of devices in accordance with the invention: (a) single radius, (b) variable radius, (c) spiral, (d) straight, and (e) angular.

One side of a device 100 in accordance with the invention is depicted in FIG. 1*a*. The device 100 illustrated therein includes a substrate 102. In one embodiment of the invention, the substrate 102 has a generally flat, circular shape. The substrate 102 may also have shapes other than circular, such as for example elliptical or square.

Figure 2A:
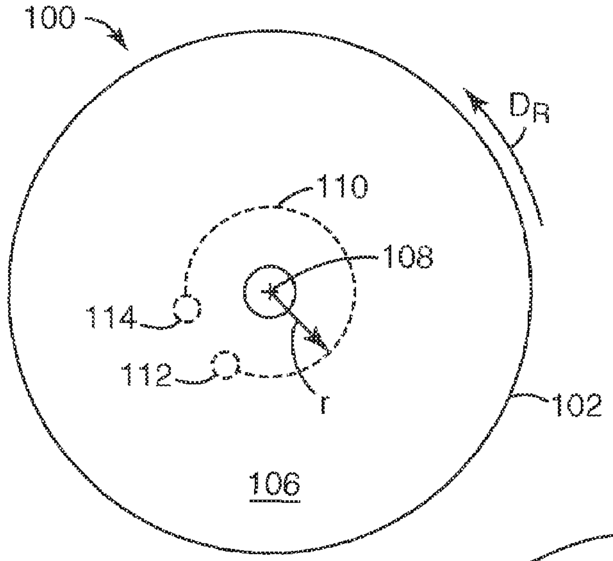
FIGS. 2*a, b, c, d*, and *e* are plan views of the opposing sides of the devices depicted in FIGS. 1*a, b, c, d*, and *e*.
Figure 2B:
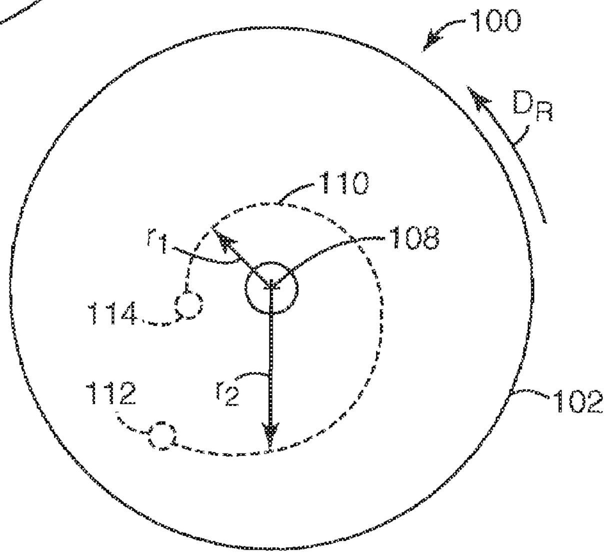
Figure 2C:
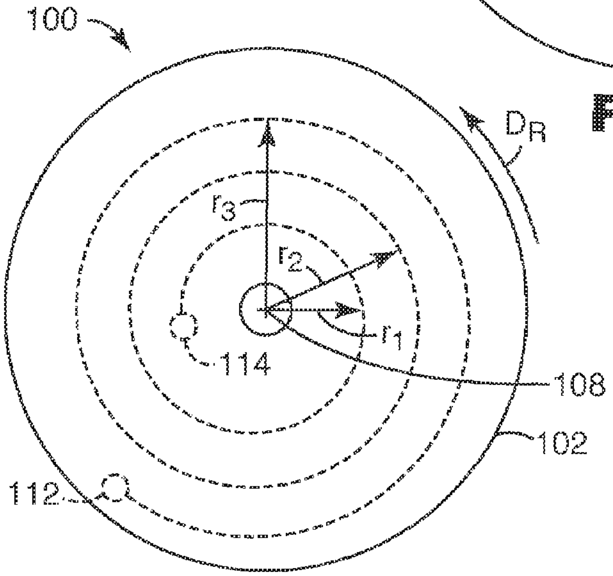
Figure 2D:
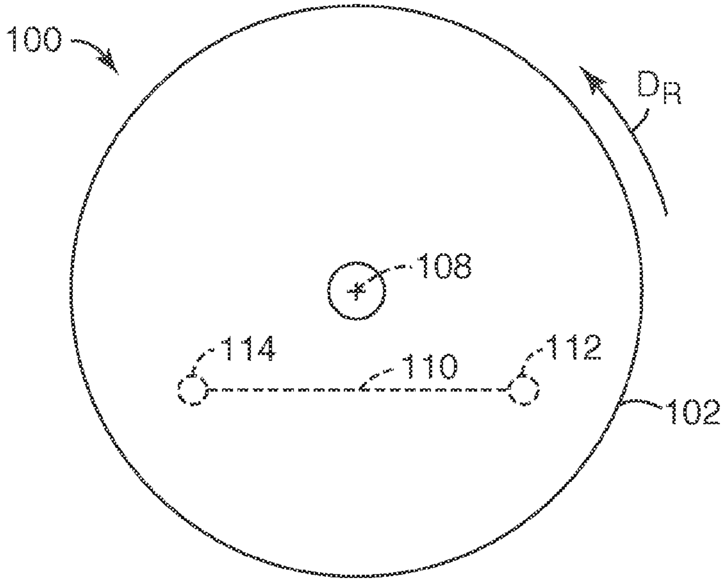
Figure 2E:
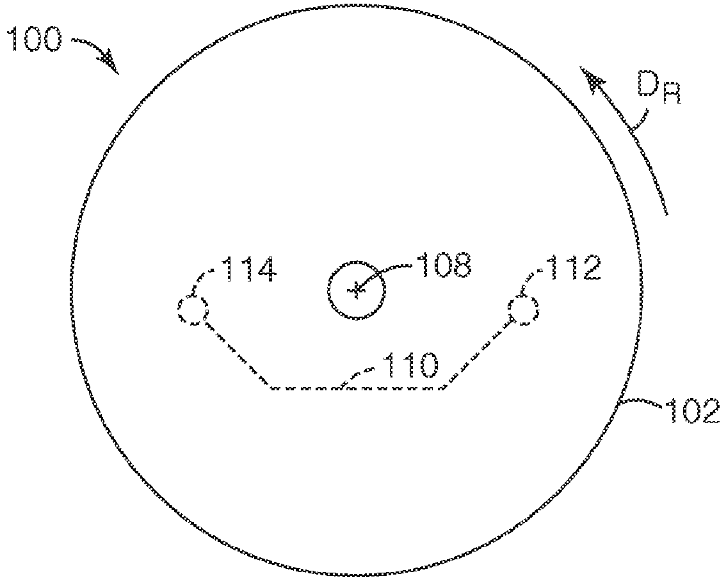

The substrate 102 includes a first major surface 104 and a second major surface 106, depicted in FIG. 2*a*. It should be understood by one of skill in the art having read this specification, that features that are formed in the substrate 102 may be formed on either the first major surface 104, the second major surface 106, or any combination thereof.

In the description of a device 100 in accordance with the invention, the relative terms "top" and "bottom" may be used. It should be understood that these terms are used in their relative sense only. For example, in connection with the first major surface 104 and the second major surface 106 of the substrate 102, the phrases "top" and "bottom" may be used to signify opposing surfaces of the substrate 102. Note that in use, the orientation of the device is irrelevant and description of the "top" or "bottom" of the device is not meant to limit the invention or the use thereof in any way.

The thickness of the substrate 102 may vary depending on a number of factors, including but not limited to the depth of features contained within the substrate 102. In one embodiment of the invention, the substrate 102 is about 0.1 mm to about 100 mm thick. In another embodiment, the substrate 102 is about 1 mm to about 4 mm thick.

The size of the substrate 102 may also vary depending on a number of factors, including but not limited to the number, types, and sizes of the features formed therein, the system that is to be used to control the device, and the size of the sample to be analyzed. In general, in an embodiment where the substrate 102 is circular in shape, the diameter of the substrate 102 is from about 50 mm to about 500 mm. In another embodiment, the substrate 102 has a diameter from about 80 mm to about 120 mm.

The substrate 102 may be made of any material that one of skill in the art, having read this specification, would recognize as appropriate for such a device. Examples of such materials include but are not limited to polymers, such as thermoplastics including polyolefins, polypropylene, polycarbonates, high-density polyethylene, polymethyl methacrylates, polystyrene, polytetrafluoroethylene (Teflon® available from Dupont), polysiloxanes or combinations thereof. In one embodiment of the invention, the substrate 102 is made of polypropylene.

The substrate 102, containing the various features formed therein can be fabricated by any method known to those of skill in the art, having read this specification. Examples of such methods of fabricating the features formed within substrate 102 include, but are not limited to injection molding, machining, micro-machining, extrusion replication, stamping, laser ablation, reactive ion etching or combinations thereof.

A device 100 of the invention also includes a hub defining a central axis of rotation 108 for the substrate 102. Devices 100 of the invention are arranged such that rotation of the device 100 about the central axis of rotation 108 facilitates the transfer or movement of materials within and between different features of the device 100. The arrow $D_R$ in FIGS. 1*a, b, c, d*, and *e* depicts rotation of the device 100 about the central axis of rotation 108. One of skill in the art, having read this specification, will understand that the device could also be rotated in the direction opposite that designated in FIGS. 1*a, b, c, d*, and *e*.

A device 100 in accordance with the invention also includes an unvented channel 110. Examples of various configurations of the unvented channel 110 an be seen in FIGS. 1*a, b, c, d*, and *e*. The opposing side, the second major surface 106 of the exemplary devices shown in FIGS. 1*a, b, c, d*, and *e* are depicted in FIGS. 2*a, b, c, d*, and *e* respectively. The unvented channel 110 is generally formed within the first major surface 104, the second major surface 106, or a combination thereof. In the embodiment depicted in FIGS. 1*a, b, c, d*, and *e*, and in FIGS. 2*a, b, c, d, e*, the unvented channel 110 is formed in the first major surface 104, as depicted by the solid line on FIGS. 1*a, b, c, d*, and *e* and the dotted line on FIGS. 2*a, b, c, d*, and *e* signifying that the unvented channel 110 is formed on or into the hidden or opposing side of the substrate 102 shown in FIGS. 2*a, b, c, d*, and *e*.

As used herein, the word "unvented" in the phrase "unvented channel" 110 means that, when filled with liquid, a vacuum can be created in the channel by the displacement of a portion of fluid from the channel. In certain embodiments, the vacuum that can be created in the channel is filled by gas from within the device, as opposed to gas from outside the device. For example, as fluid is displaced from the channel (e.g. by rotating the device) and enters a connection structure, the gas in the connection structure will be forced into the channel by the incoming fluid and enter the vacuum in the channel that was created by the displacement of fluid. Unvented in this sense it differs from a vented system where gas from outside the device is drawn into the channel by the displacement of fluid from the channel. A vented system will also generally include a vent to prevent a vacuum from being formed in the channel by the displacment of fluid. Use of the word "unvented" does not mean that the channel could not contain a vent, rather it means that the channel exhibits the above-described characteristics of an unvented or sealed system In one embodiment of the invention, the unvented channel 110 generally follows the arc of the substrate 102. In one exemplary embodiment, where the substrate 102 has a generally circular shape, the unvented channel 110 can have an arc that generally follows the arc of the substrate 102, i.e., is circular or concentric about the center of the substrate. The length of the unvented channel 110 may be selected based on a number of factors, including but not limited to, the purpose for the unvented channel 110, and the size of the substrate 102. In an embodiment where the unvented channel 110 is to be used for isoelectric focusing (IEF), the length of the unvented channel 110 may depend at least in part on the pH sensitivity desired in the separation i.e. the number of pH fractions desired, and the particular types of samples that are to be separated.

The length of the unvented channel 110 may be characterized in terms of the angular size of the arc formed by the unvented channel 110 when measured relative to the axis of rotation 108 about which the device 100 is rotated during use. For example, the unvented channel 110 may form an arc of about 10 degrees or more, alternatively about 180 or more, when measured relative the axis of rotation 108 about which the device 100 is rotated during use. Alternatively, the unvented channel 110 can form a longer arc about the device 100. For example, the unvented channel 110 may form an arc of about 320 degrees or more when measured relative to the axis of rotation 108 about which the device 100 is rotated during use. It should also be understood that in some instances the unvented channel 110 could extend more than 360 degrees about the device 100. When characterized in terms of an angular arc, the size of the device 100 will also be a factor in determining the path length of the unvented channel 110.

The device may also be characterized by the distance of the unvented channel 110 to the axis of rotation 108. The distance in this context refers to the distance of the center of the unvented channel 110 to the axis of rotation 108. This distance is depicted as radius r in FIG. 1*a*. In one embodiment of the invention, the unvented channel 110 has a radius of at least about 10 mm. In another embodiment, the unvented channel 110 has a radius of about 10 mm to about 120 mm. In another embodiment, the unvented channel 110 has a radius of about 20 mm to about 50 mm.

Figure 1B:
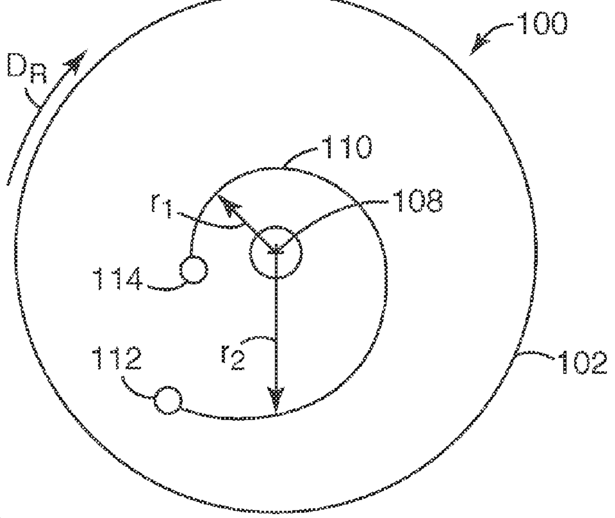
Figure 1C:
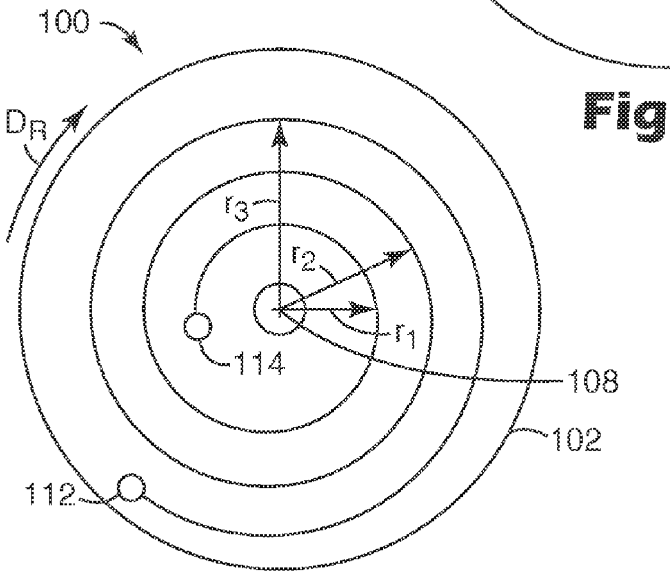

In one embodiment of the invention, the radius is not constant over the entire length of the unvented channel 110. In one embodiment, the radius can increase over the length of the unvented channel 110. One example of a device of the invention having an increasing radius ($r_2>r_1$) is seen in FIG. 1*b*. Such a device can also be characterized as having a decreasing radius, i.e., $r_2<r_1$ depending on the relative comparison. A device with a non-constant radius can also form a spiral unvented channel 110. An example of such a device is seen in FIG. 1*c*. In this example $r_1<r_2<r_3$.

Figure 1D:
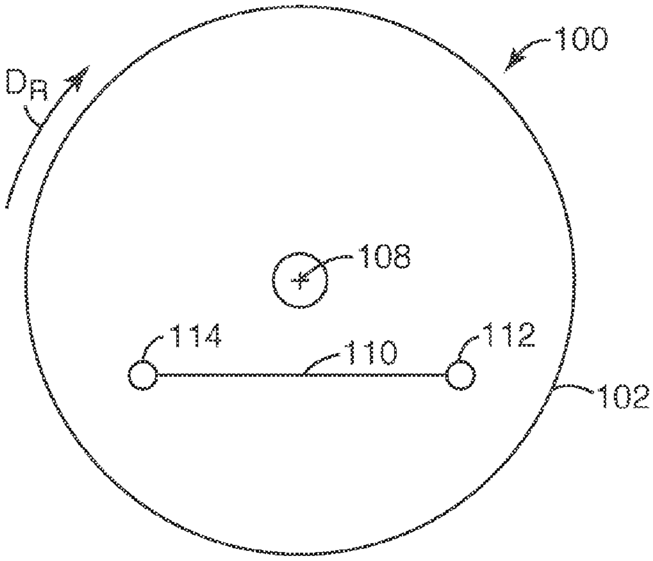
Figure 1E:
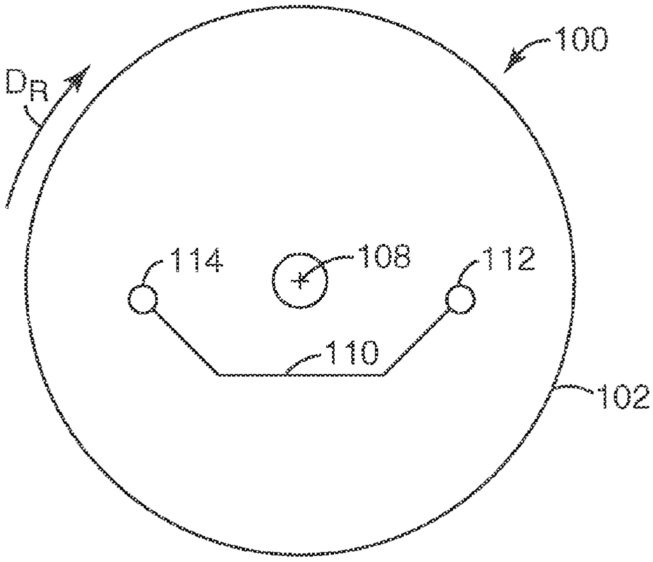

In another embodiment, depicted in FIG. 1*d*, the unvented channel may follow a straight path running, for example, roughly parallel to the axis of rotation 108 along a major surface of the substrate. Alternatively, the channel may be in the form of a series of straight sections arranged concentrically about the center of the substrate, as shown in FIG. 1*e*, or with a varying distance from the center, as discussed above.

The depth and width of the unvented channel 110 may depend at least in part on the size of the substrate 102, the length of the unvented channel 110, the size of the sample, or some combination thereof. In general, the depth of the unvented channel 110 is from about 10 μm to about 2000 μm. In one embodiment the depth of the unvented channel 110 is from about 100 μm to about 500 μm. Embodiments having deeper unvented channels 110 can utilize increased sample loading as opposed to unvented channels 110 that are not as deep. However, an increased channel depth can lead to increased Joule heating due to increased current for a set electric field strength. Generally, increased Joule heating is undesirable. Therefore in one embodiment of the invention, optimization of the desired sample size with the amount of Joule heating that can be tolerated will dictate at least in part, the dimensions of the unvented channel 110. In general, the width of the unvented channel 110 is from about 10 μm to about 2000 μm. In one embodiment the width of the unvented channel 110 is from about 100 μm to about 1000 μm.

The sides or surfaces of the unvented channel 110 can have a number of different characteristics, including smooth surfaces, rough surfaces, undulating surfaces, straight sides, or slanted sides for example. One of skill in the art, having read this specification, will also understand that these characteristics, or combinations thereof may offer various advantages or disadvantages based on different uses of the devices.

In one embodiment of a device 100 in accordance with the invention, the unvented channel 110 includes first 112 and second 114 sample wells. The first 112 and the second 114 sample wells may generally be described as compartments on both ends of the unvented channel 110. The first 112 and second 114 sample wells can have numerous functions, for example: introduce samples to the device 100, introduce one or more electrodes to the device 100, introduce reagents or solutions to the device 100, or any combination thereof. In one embodiment of the invention, the first 112 or the second 114 sample well is utilized to introduce a sample into the device 100. In another embodiment, one or more of the first 112 and/or the second 114 sample wells can be used to introduce two different solutions, and introduce two electrodes into the device 100.

In one embodiment, the first 112 and second 114 sample wells are configured to allow a user to introduce a sample, reagents or solutions into the device 100 using a pipette or syringe. In another embodiment of the device, the first 112 and second 114 sample wells are also configured to function with an integrated electrode that is described in greater detail below.

Figure 3:
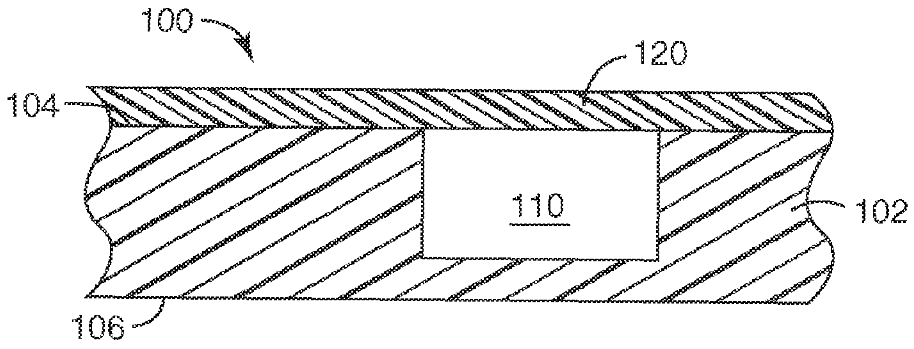
FIG. 3 is a cross-sectional view of a portion of a device in accordance with the invention.

In one embodiment of the invention, the features contained in the substrate 102 are sealed or covered. FIG. 3 depicts a cross-section of a portion of a device 100, and an exemplary method for sealing the device 100. The device 100 includes the substrate 102 having a first major surface 104 and a second major surface 106 in which at least the unvented channel 110 is formed. In this embodiment of the invention, a cover film 120 is applied to the first major surface 104 of the substrate 102. It should be understood by one of skill in the art, having read this specification, that the cover film 120 could be applied only to the areas of the first major surface 104 containing features or to the entirety of the first major surface 104. One of skill in the art, having read this specification, will also understand that either the first major surface 104, the second major surface 106, or both could be covered with cover film 120 depending on whether or not features have been formed within both surfaces or only within one of the surfaces.

In one embodiment of the invention, the cover film 120 has a thickness of about 50 μm to about 1000 μm. In another embodiment, the cover film 120 has a thickness of about 100 μm to about 250 μm. The cover film 120 can be made of any material that one of skill in the art, having read this specification, would find appropriate. Examples of such materials include but are not limited to polyolefins, polypropylene, polycarbonates, high-density polyethylene, polymethyl methacrylates, polystyrene, polytetrafluoroethylene (Teflon® available from Dupont), polysiloxanes, and combinations thereof. In one embodiment, the substrate 102 is sealed with transparent polyolefin pressure sensitive silicone adhesive.

The cover film 120, which acts as a sealing membrane, can, but need not include an adhesive, such as a pressure sensitive adhesive, disposed on a backing (such as a backing that is transparent to electromagnetic energy of selected wavelengths). In one embodiment, the adhesive is selected such that it adheres well to materials of which conventional analytical receptacles are made (such as polyolefins, polystyrene, polycarbonates, or combinations thereof), maintains adhesion during high and low temperature storage (e.g., about −80 degrees Celsius. to about 150 degrees Celsius) while still providing an effective seal against sample evaporation, does not substantially dissolve in or otherwise react with the components of the biological sample mixture, or some combination thereof. One of skill in the art, having read this specification, would understand that some of these considerations may be important for some applications and some may not be important. In one embodiment, the adhesive does not interfere (e.g., bind proteins, dissolve in solution, etc.) with any processes performed in the device 100. Exemplary adhesives can include those typically used on cover films of analytical devices in which biological reactions are carried out. Such adhesives include, but are not limited to poly-alpha olefins and silicones, for example, as described in International Publication Nos. WO 00/45180 (Ko et al.) and WO 00/68336 (Ko et al.), the disclosure of which is incorporated herein by reference.

Figure 4:
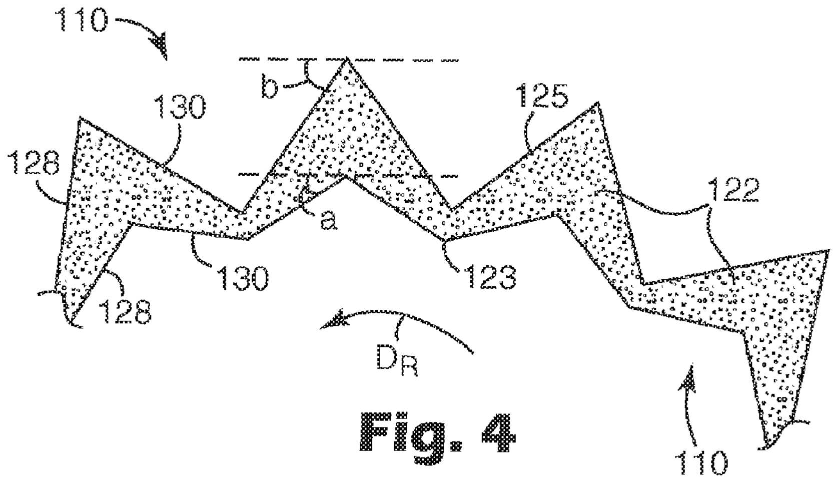
FIG. 4 is a plan view of a portion of an unvented channel in accordance with the invention.

In one embodiment of a device 100 of the invention, the unvented channel 110 includes a plurality of connected compartments 122. FIG. 4 depicts a portion of one embodiment of an unvented channel 110 that includes a plurality of connected compartments 122. The inner radius 123 of the unvented channel 110 may contain characteristics such as serrations or may not. The outer radius 125 of the unvented channel 110 may contain characteristics such as serrations or may not. The unvented channel 110 may be characterized by abrupt angles, or alternatively may be curved. In this embodiment, the structure of the unvented channel 110 is generally referred to herein as "compartmentalized."

In one embodiment of the invention, each of the plurality of connected compartments has a volume of at least about 1 picoliter (pL). In another embodiment, each of the plurality of connected compartments has a volume of less than about 100 μl. In one embodiment of the invention, at least one of the plurality of connected compartments 122 has a different volume than the other of the plurality of connected compartments 122. Such an embodiment may allow for variation in the samples collected. This may be able to save the user time by focusing only the sample of interest. This may also aid in placing more than one unvented channel 110 on a single device 100.

As seen in FIG. 4, each of the plurality of connected compartments 122 has a leading edge 128 and a trailing edge 130. The trailing edges 130 are the sides of the connected compartments 122 that face the direction of rotation $D_R$. The leading edges 128 are the other side of each of the respective connected compartments 122, or the side facing away from the direction of rotation $D_R$. The angle of the leading edge 128 of the inner radius 123 of the unvented channel 110 to the center of gravity (defined by a in FIG. 4) is generally in the range of from about 10 degrees to about 90 degrees. In one embodiment, the angle of the leading edge 128 of the outer radius 125 of the unvented channel 110 (defined by b in FIG. 4) to the center of gravity is about 45°. In one embodiment, the angle b is greater than or equal to a. In another embodiment, the angle b is equal to a. In one embodiment, the angles of the trailing edge 130 to the inner radius 123 and the outer radius 125 are dictated by a and b, and in one embodiment are the same as a and b. In one embodiment, a serrated channel that is created with the angles of the leading edge 128 and the trailing edge 130 may serve to reduce fluid inertia during device rotation in the unvented channel 110.

Figure 5A:
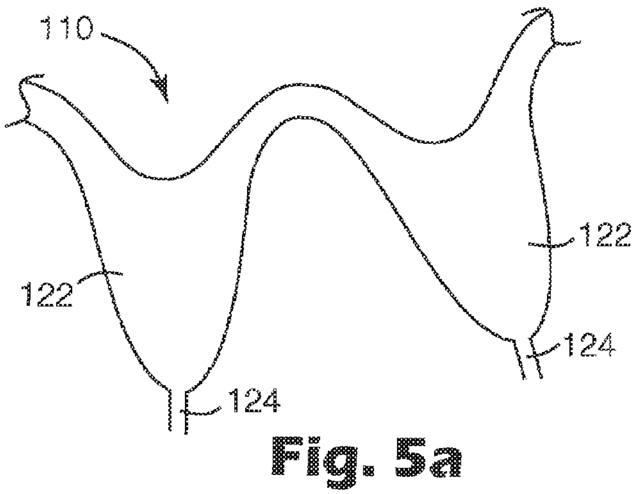
FIGS. 5*a, b, c, d, e, f, g*, and *h* depict exemplary designs for the unvented channel.

FIG. 5*a* depicts another exemplary design for the unvented channel 110. In this embodiment, transitions between the plurality of the connected compartments 122 of the unvented channel 110 are smooth. Such an embodiment may limit the effects of Joule heating within the unvented channel 110.

Figure 5B:
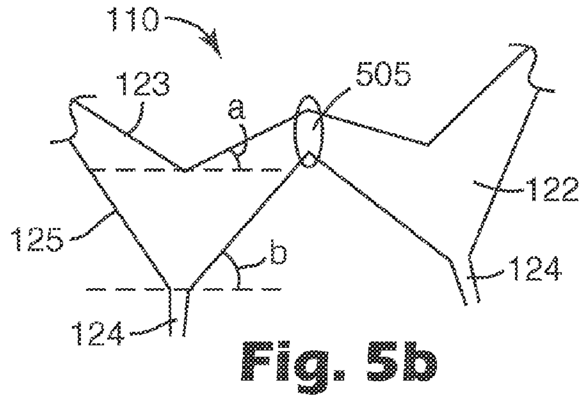

FIG. 5*b* depicts another exemplary design for the unvented channel 110. This embodiment depicts a pinch point 505. A pinch point 505 generally refers to the narrowest region of the unvented channel 110 between two connected compartments 122. It should be understood by one of skill in the art, having read this specification, that the dimensions of the pinch points 505 can be dictated at least in part by the angles of the leading edge 128 of the inner radius 123 (i.e. the side of the channel closer to the center of rotation of the substrate) and the outer radius 125 (the side of the channel farther from the center of rotation of the substrates) to the central axis of rotation 108. In one embodiment of the invention, a smaller pinch point 505 can provide more effective separation when using a device of the invention for protein separation. However, as the dimensions of the pinch point 505 get smaller, the effects of Joule heating increases. In one embodiment, the pinch point 505 has a diameter of about 200 μm or less. In another embodiment, the pinch point 505 has a diameter of about 10 μm.

In one embodiment of the invention, the plurality of the connected compartments 122 function to collect parts of the sample that are then passed through the collection area 124 (See FIGS. 5*a* and *b*). Typically, the sample then goes from the collection area 124 to at least one other feature of the device, for example, via a connection structure or channel.

Figure 5C:
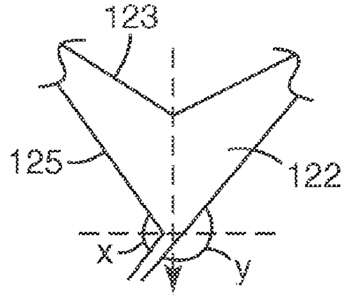
Figure 5D:
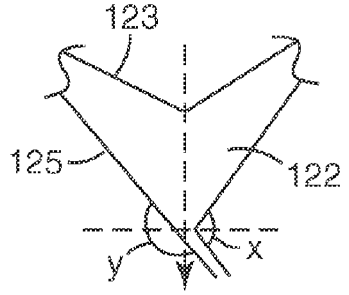
Figure 5E:
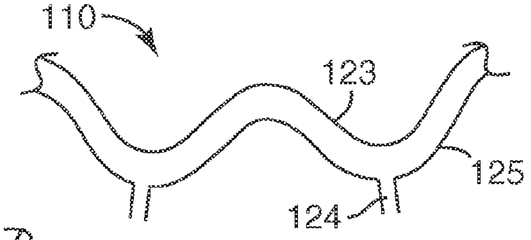

As shown in FIGS. 5*c* and *d*, the collection areas may be configured so that the sample passes into a connection structure or channel or otherwise exists the compartment(s) at any of a variety of angles. For example, the angles identified in FIGS. 5*c* and *d* as angles X and Y located between the collection area 124 and the outer radius 125 may be about equal, (see e.g. FIG. 5*b*), or the angles may be different such that X<Y or X>Y, as shown in FIGS. 5*c* and *d*, respectively. In one embodiment, either X or Y is about 180°.

In another embodiment of the invention, the unvented channel 110 does not include a plurality of connected compartments, but includes a structure that has a varying radius from the central axis of rotation 108. Such an embodiment can be described as being serpentine. In such an embodiment, the distance of the middle of the unvented channel 110 to the central axis of rotation 108 undulates between a minimum and a maximum. This type of a serpentine unvented channel 110 may or may not have a constant distance from the central axis of rotation 108 to the inner radius 123 and a greater constant distance from the central axis of rotation 108 to the outer radius 125 of the unvented channel 110.

Figure 5F:
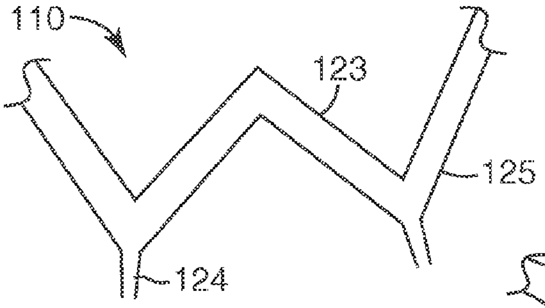
Figure 5G:
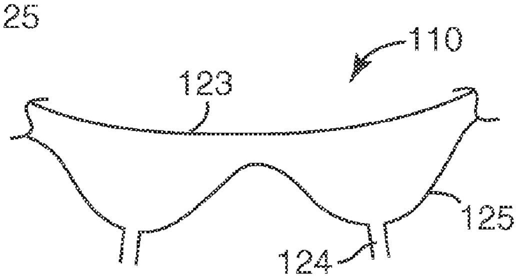
Figure 5H:
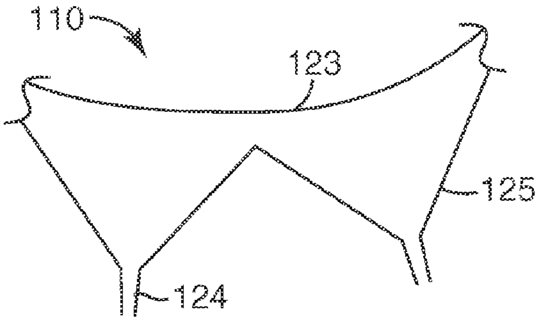

In one implementation of the invention, the channel wall closer to the center (i.e. the inner radius) varies in distance from the center of substrate. The distance to the center may, for example, vary or oscillate between a set minimum and maximum to create an undulating or zig-zag type pattern as shown in FIGS. 5*f* and *g*. The channel wall that is farther from the center (i.e. the outer radius) may likewise vary or oscillate between a desired minimum and maximum value. The inner and outer radii may, as shown in FIGS. 5*f* and *g*, fluctuate by the same amount, in which case the width or cross-sectional area of the channel would remain relatively constant. Alternatively, the outer and inner radii may fluctuate by different amounts, which results in alternating pinch points (areas where the channel narrows) and compartments. An example of such an embodiment is shown in FIG. 4 and in FIGS. 5*a* and *b*, where the inner radius fluctuates by a lesser amount than the outer radius. In yet another embodiment, depicted in FIGS. 5*g* and *h*, the inner radius may remain relatively constant while the outer radius fluctuates, or vice versa.

In one embodiment of the invention, the unvented channel 110 can be used to carry out isoelectric focusing (IEF) in which the connected compartments 122 function to create different pH bins for separation of proteins from a sample. In such an embodiment, at least one solution besides the sample to be separated can be added to the unvented channel 110. In use, this at least one solution can be added before the device 100 is obtained by the ultimate user, or can be added by the user. In an embodiment where the unvented channel 110 is used for IEF, the separated protein fractions can be removed from the device 100 for further analysis, or the device 100 can be configured so that further analysis can be carried out on the device 100 itself.

In an embodiment of the invention where the unvented channel 110 is to be used for IEF of proteins, the unvented channel may be, but need not be, surface modified.

In one embodiment, virtually any surface of any feature within the device can be modified to alter some property thereof. Examples of properties that can be altered include, but are not limited to, surface energy, hydrophobicity, hydrophilicity, or reactivity to specific moieties. In one embodiment, the surface energy of at least one surface of at least one feature is increased. An example of a material that can be used to modify the surface to increase the surface energy includes diamond-like glass. Details regarding diamond-like glass can be found in WO 01/67087, the disclosure of which is incorporated herein by reference.

Figure 6A:
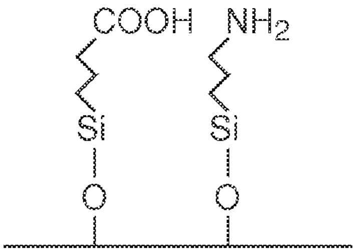
FIGS. 6*a* and *b* depict examples of immobilization schemes for creating pH gradients.
Figure 6B:
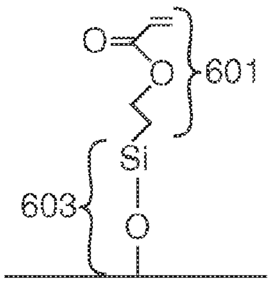

In one embodiment, the surface of the unvented channel 110 can be modified to create a pH gradient when a solution is added to the unvented channel. When the unvented channel is surface modified to allow a pH gradient to be formed in the device, the surface modification is referred to herein as an "immobilized pH gradient." Any method known to those of skill in the art, having read this specification, can be used to create an immobilized pH gradient. FIGS. 6*a* and 6*b* depict two examples of surface modifications that can be utilized to create an immobilized pH gradient. The example depicted in FIG. 6*a* includes surface modifying the unvented channel by silanating the polymeric surface with a trimethylsilane plasma treatment. An acryloxypropyltrimeth-oxysilane (represented by 601 in FIG. 6*a*) is first bonded to the surface Si—OH groups (represented by 603). Immobiline™ (Amersham Bioscience, Sunnyvale Calif.) monomers can then be reacted with the acrylate functionality of 601 to graft the necessary molecules to create a pH gradient. Other silane chemistries that have functionalities that react to the amide group may also be used. FIG. 6*b* depicts another exemplary method of creating an immobilized pH gradient that includes reacting silanes having different functionality (and therefore different pKa values) with the plasma treated surface. This method does not require the additional step of immobilizing Immobiline™ to the channel surface.

Other Features

In one embodiment, a device of the invention may contain features besides those discussed above. Examples of such other features include, but are not limited to, chambers, connection structures, valves, and analysis structures. It should be understood by those of skill in the art, having read this specification, that such other features can be formed in a manner similar to that of the unvented channel.

Figure 7A:
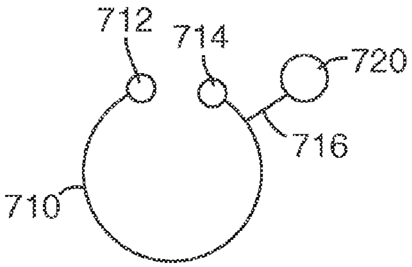
FIGS. 7*a, b, c, d, e, f, g, h*, and *i* show different geometries: (a) sample chamber (b) sample chamber with valve (c) sample chamber with two valves and collection bin (d) sample chamber with two valves and connection to capillary electrophoresis on the disk (e) as with 7*d* with single capillary, (f) multiple sample chambers, (g) sample injection port removed from sample well, (h) sample straight channel with connection structure, and (i) angular channel with connection structures.

Examples of devices that include some such features can be seen in FIGS. 7*a, b, c, d, e, f, g, h*, and *i*. The devices in FIGS. 7*a, b, c, d, e, f, g, h*, and *i* depict only the features that would be formed in such an exemplary device, not the device (i.e., the substrate) itself.

The exemplary device in FIG. 7*a* includes an unvented channel 710, a first sample well 712, a second sample well 714, at least one compartment connection structure 716 and at least one chamber 720.

The unvented channel 710, first sample well 712, and second sample well 714 in accordance with the invention may include some or any combination of the characteristics that were discussed previously. The plurality of compartment connection structures 716 function to connect the plurality of connected compartments (not specifically shown in FIG. 7*a*) of the unvented channel 710 to the plurality of chambers 720. In embodiments where the unvented channel 110 is not made of a plurality of connected compartments, such as the exemplary serpentine unvented channel, the plurality of connected compartments generally contact the outer radius 125 of the unvented channel 110 where the outer radius 125 is farthest from the central axis of rotation 108. Generally, the physical characteristics of the compartment connection structures 716, such as length, depth, width, etc. will be chosen to be on the same scale as the dimensions of the unvented channel 710 and chambers 720 that they connect. The compartment connection structures 716 cross-section geometries may be for example, trapezoidal, circular, rectangular, or any variation on these geometries. The surfaces on the compartment connection structures 716 may also be modified to change the surface characteristics such as to prevent or promote capillary wicking of the solution or perform modifications to the chemical solution.

The plurality of chambers 720 may generally function to contain a sample that has been transferred from the connected compartments (not shown here) of the unvented channel 710 through the compartment connection structures 716. The chambers 720 can, but need not, also serve as a reaction well, a cooling or heating region, a holding area, or any combination thereof. Generally, the physical characteristics of the compartment connection structures 716, such as the length, depth, width, etc. will be chosen to be on the same scale as the dimensions of the unvented channel 710 and chambers 720 that they connect. The chambers 720 can, but need not be functionalized to perform chemical reactions or modifications to the sample. In one embodiment, one connected compartment (not shown in FIG. 7*a*) may be connected to more than one chamber 720 in series. This could allow a sample to be processed under more than one set of conditions.

In one embodiment of the invention, the plurality of chambers 720 can function as reaction wells. In such an embodiment, the chambers 720 are generally pre-filled with the reagents for the desired reaction or reactions. One example of a reaction that can be carried out in a chamber 720 includes denaturation of proteins. In this example, the reagents necessary for denaturing proteins can be pre-loaded into the chambers 720 before the ultimate user obtains the device or may be loaded by the user.

In another embodiment of the invention, the plurality of chambers 720 can function as a protein digestion well where the protein sample is digested with a protease, e.g. trypsin, to give the resulting peptides.

In an embodiment where the plurality of chambers 720 function as a heating region, any method known to those of skill in the art, having read this specification, can be used to heat the chambers. An example of which can be found in WO 02/00347, the disclosure of which is incorporated herein by reference. In yet another embodiment, the plurality of chambers 720 can function both as reaction wells and as a heating region.

Figure 7B:
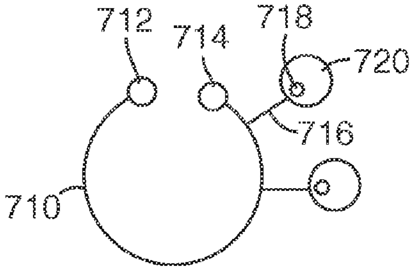

Another exemplary embodiment of the invention is depicted in FIG. 7*b*. The device in FIG. 7*b* includes all of the features of FIG. 7*a* (numbered the same) as well as at least one compartment valve 718 within or in connection with the chamber 720. The features discussed above with respect to FIG. 7*a* may have some or any combination of the characteristics and/or functions discussed above. The compartment valve 718 functions to control the flow of fluid from the plurality of connected compartments of the unvented channel 710 to the chamber 720. Exemplary configurations and functioning of compartment valves 718 will be discussed in greater detail below.

Figure 7C:
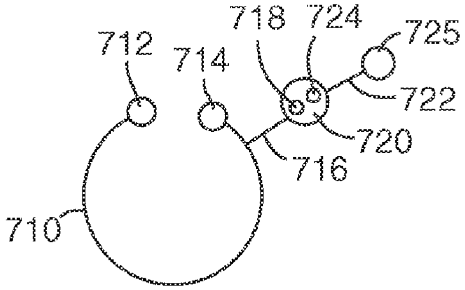

FIG. 7*c* depicts another exemplary embodiment of a device in accordance with the invention. The device features depicted in FIG. 7*c* include all of the features of the device depicted in FIG. 7*b* (numbered the same) as well as at least one chamber valve 724, at least one chamber connection structure 722, and at least one collection bin 725. The features discussed above with respect to FIGS. 7*a* and *b* may have some or any combination of the same characteristics and/or functions. In this embodiment, the at least one chamber valve 724 functions to control the flow of fluid from the chamber 720 to the collection area 725.

Figure 7D:
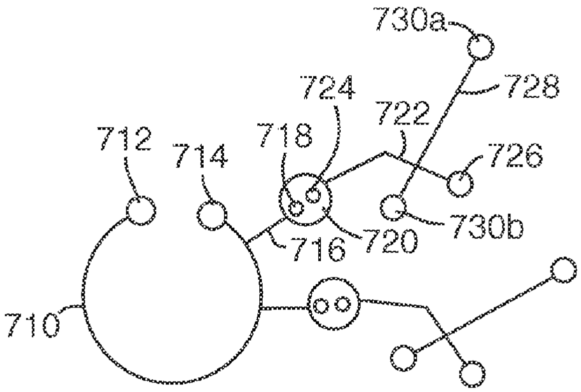

The exemplary device depicted in FIG. 7*d* includes all of the features of the device depicted in FIG. 7*c* (numbered the same) as well as at least one measurement electrode 726, at least one channel 728 and its accompanying electrodes 730*a* and 730*b*. The features discussed above with respect to FIGS. 7*a, b*, and *c* may have some or any combination of the same characteristics and/or functions. In one embodiment, the sample chamber 720 contains a measurement electrode that can be configured to monitor the pH of the solution within the device in sample chamber 720. In one embodiment, the measurement electrode is an integrated element that can be an ion sensitive field effect transistor (ISFET). Other exemplary characteristics that the measurement electrode can monitor include, but are not limited to, temperature, dissolved oxygen, and dissolved ion concentration (to measure desalting for example).

This embodiment also includes channel 728. The channel 728 may, but need not, be configured to carry out capillary electrophoresis. Associated with channel 728 are its electrodes 730*a* and 730*b*. Exemplary methods and details about forming, utilizing and designing channels 728 for capillary electrophoresis can be found in U.S. Pat. No. 6,532,997, the disclosure of which is incorporated herein by reference.

As seen in FIGS. 7*a, b, c*, and *d*, devices of the invention may also include connection structures that serve to connect one feature of the device to another. Examples of connection structures include, but are not limited to, compartment connection structures 716 and chamber connection structures 722. Generally, the transport of the fluids from one feature to another through the connection structure is accomplished by rotating the device about its central axis. Rotational speeds of the devices required to obtain a complete transfer of the fluid from one feature of the device to the other may vary depending on a variety of factors, including but not limited to, the size of the features, the geometry of the features, the viscosity of the fluid, surface property differences between the solution and substrate, the type of valve in the connection structure (discussed below), speed, acceleration and time of rotation, or any combination thereof.

In one embodiment of the invention, a rotational speed of about 2000 rpm or higher, in some instances about 3000 rpm or higher, and in some instances about 4000 rpm or higher may be useful for transporting the fluid from one feature to another. The time necessary for transfer of the fluids will also depend on some of the same factors discussed above and the rotation speed. In one embodiment of the invention, the device can be rotated for at least about 0.1 seconds at 1 RPM, and in another embodiment for at least about 600 seconds at 10,000 RPM. In another embodiment, the device can be rotated for about 3,600 seconds at 20,000 RPM.

Figure 7E:
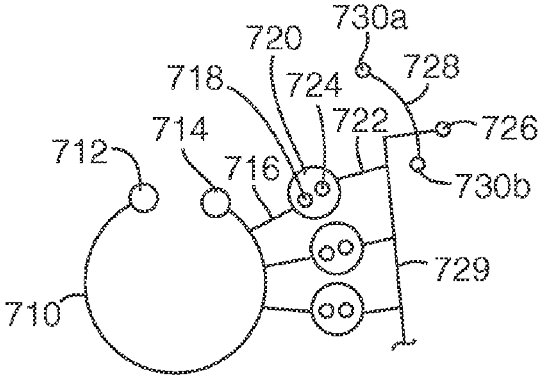

Another exemplary embodiment of the features of a device of the invention is depicted in FIG. 7*e*. The device in FIG. 7*e* has the same features as that of FIG. 7*d*, but has a single channel 728. In one embodiment, the device in FIG. 7*d* has one channel 728 for every chamber 720 on the device. Alternatively, the device depicted in FIG. 7*e* has one channel 728 to which all of the chamber connection structures 722 of the chambers 720 are connected via a channel connection structure 729.

Figure 7F:
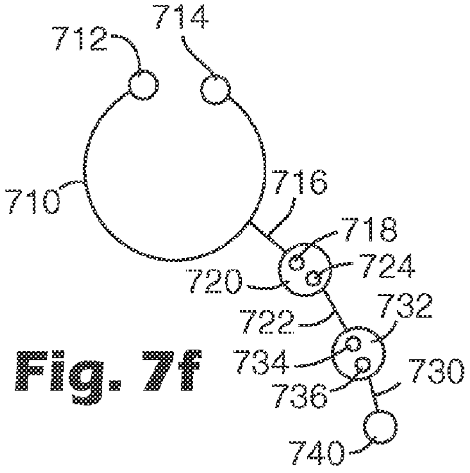

FIG. 7*f* depicts yet another exemplary embodiment of a device of the invention. The device in FIG. 7*f* has the same features as the device of FIG. 7*b* but also includes a chamber valve 724, a chamber connection structure 722, a second chamber 732 that includes a first valve 734 and a second valve 736, a bin connection structure 738 and a bin 740. In one embodiment, the second chamber 732 can function to provide a reaction well. In another embodiment, the second chamber 732 can function in the same ways as discussed with respect to the chamber 720 above.

In another embodiment of the invention, the plurality of chambers 720 can function as a protein digestion well where the protein sample is digested with trypsin to give peptides. In the second chamber 732 connected to the first chamber (not shown), the sample can be desalted in preparation for introduction into a subsequent analysis step.

Figure 7G:
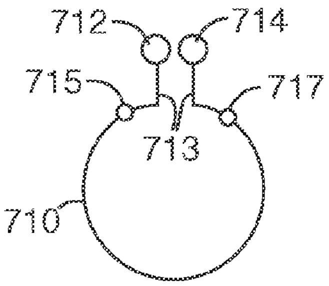
Figure 7H:
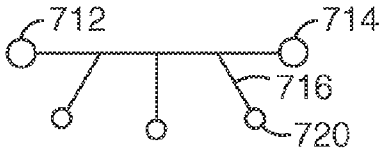
Figure 7I:
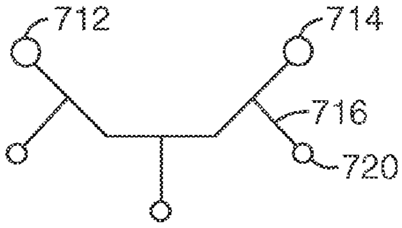

FIG. 7*g* depicts another exemplary embodiment of a device in accordance with the invention. The features in FIG. 7*g* include an unvented channel 710, a first sample compartment 715, a second sample compartment 717, a sample connection structure 713, and a first sample well 712 and the second sample well 714 at a greater radius. In one embodiment of the invention, the sample connection structure 713 is less than about 2 mm. The advantage of having the sample well 712 connected to the sample compartment 715 by the sample connection structure 713 is that the solution in sample well 712 won't spill out into the connected compartments of the unvented channel when the device is rotated. However, having the sample well removed from the sample compartment 715 (and/or 717) may result in the sample beginning to separate in the sample connection structure 713. Therefore, in an embodiment of the invention that has a sample connection structure 713, the length of the sample connection structure 713 can be considered a compromise between these two factors.

One of skill in the art, having read this specification, will understand that virtually any combination of features can be formed within the substrate 102. It will also be understood by one of skill in the art, having read this specification, that any combination of the features in any of the figures including but not limited to FIGS. 7*a-g* can be combined in any combination. It should also be understood that if so desired these features can be formed in either the first major surface, second major surface, or some combination thereof. If features are formed in both the first and the second major surface, connection between those features can be accomplished by forming the connection structures deep enough into the substrate to connect the two features.

Although the unvented channels depicted in FIGS. 7*a-i* and in FIGS. 1*a-e* are shown as a simple line following a curved, straight or angular path, it should be understood that these lines are meant to illustrate the overall structure or path of the channel, but the walls or sides of the channel (i.e. the inner and/or outer radius) may nevertheless have a serrated (jagged) or serpentine shape, as discussed above, and/or the channel may or may not have compartments and pinch points (i.e. areas where the width or cross-sectional area of the channel increases and decreases). Thus, the sides of the unvented channel 710 of FIGS. 7*c-i* and the unvented channel 110 of FIGS. 1*a-e* can have inner and outer radii with the shapes shown, for example, in FIG. 4 and FIGS. 5*a-h*, even though the channel as a whole follows a relatively smooth path.

Valve Systems

Connected compartments, chambers or connection structures of the invention can, but need not include one or more integrated valve structures. Such valve structures were referred to in FIGS. 7*a, b, c, d, e, f, g, h*, and *i* above. One example of an integrated valve structure can be seen in FIGS. 8 and 9*a*. The valve structure in this embodiment of the invention is in the form of a lip 140 that protrudes into the periphery of the connected compartment, chamber or connection structure, represented by the reference numeral 139 (referred to collectively herein as a "feature") as defined by the wall 141 (seen in FIG. 9*a*) which in a generally circular shape extends around the entire periphery of the feature 139 (with the periphery of the features 139 being depicted in a combination of solid and broken (hidden) lines in FIG. 8). It will be understood that other process chambers may have a sidewall that is broken into segments, e.g., a triangle, a square, etc.

Figure 8:
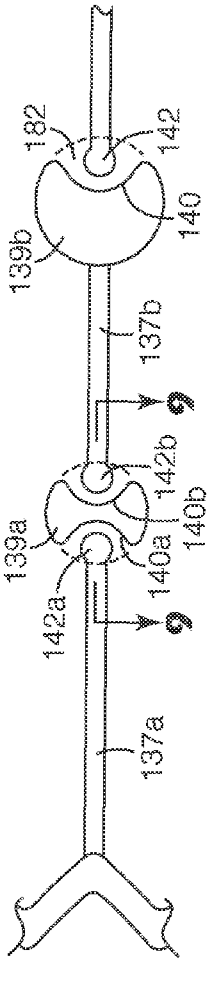
FIG. 8 is a plan view of a portion of the features of a device.
Figure 9A:
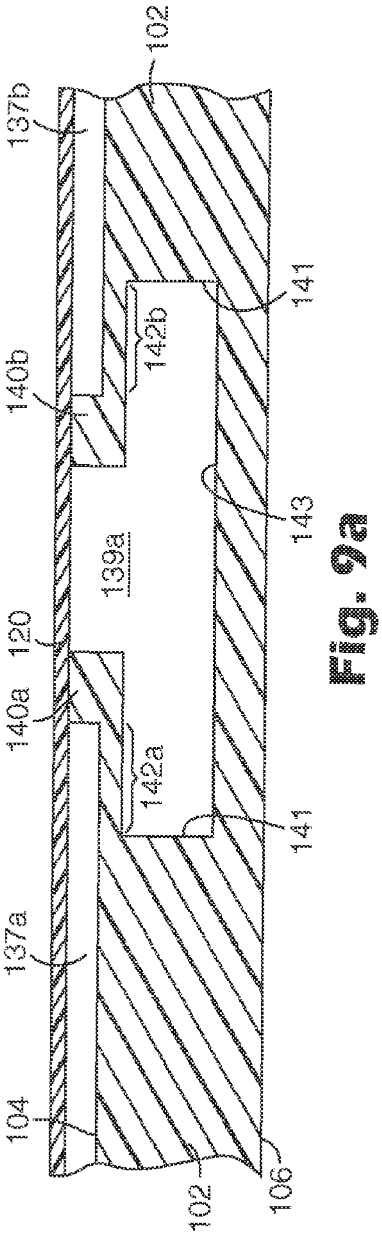
FIGS. 9*a* and *b* are cross-sectional views of a portion of a device having two valves in accordance with the invention.
Figure 9B:
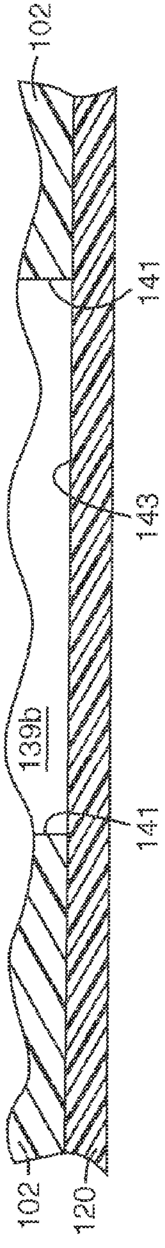

The boundaries of the feature 139 can be further defined by the bottom surface 143 of the feature 139, which in turn can be defined by the substrate 102, or the cover film 120 (as shown in FIG. 9*b*). The lip 140*a* is in the form of an undercut extension into the volume of the feature 139 as seen in, e.g., FIG. 9*a*. As a result, a portion of the volume of the feature 139 is located between the lips 140*a* and *b* and the cover film 120. The particular embodiment depicted in FIGS. 8 and 9*a* has a valve structure on both sides of the feature 139. Therefore a portion of the volume of the feature is also located between the lip 140*b* and the cover film 120.

A portion of the connection structure 137*b* extends into the lip 140*b*, with the opposite end of the connection structure 137*b* being located in the next feature 139*c*. Where the connection structure 137*b* extends onto the lip 140*b*, a thin area 142*b* is formed with a reduced thickness relative to a remainder of the lip 140*b*. A similar thin area 142*a* is also formed on the opposite end of the feature 139 where a portion of the connection structure 137*a* extends onto the lip 140*a*.

When an opening is provided in the lip 140 or within the thin area 142 occupied by the connection structure 137*b*, sample materials in the feature 139*a* can move into the connection structure 137*b* for delivery to feature 139*b*. In the absence of an opening in the lips 140*a* and *b*, movement of materials into feature 139*a* or into 139*b* is prevented by the lips 140*a* and *b* which otherwise seal against the cover film 120 to prevent the flow of sample materials out of feature 139*a* in this case.

Openings in the lip 140 can be formed by any suitable technique or techniques. For example, the lip 140 may be mechanically pierced, ablated with laser energy, etc. In other embodiments, a valve structure may be incorporated in the lip 140 such that when the valve structure is opened, materials can move from the feature 139*a* into the connection structure 137*b*. Examples of some valve structures may include foams, shape memory materials, etc. as described in, e.g., U.S. patent application Publication No. 20020047003, the disclosure of which is incorporated herein by reference.

The reduced thickness of the lip 140 in the area 142 occupied by the connection structure 137*b* may provide a number of advantages. It may, for example, limit the location or locations in which the lip 140 may be easily pierced or otherwise deformed to provide the desired opening, i.e., the thicker portions of the lip 140 surrounding the area 142 may be more resistant to deformation by any of the techniques that could be used to form an opening there through. Another potential advantage of the area 142 of reduced thickness is that it can be molded into the substrate 102 along with, e.g., the other features and connection structures.

Regardless of the exact nature of the valve structure used, one advantage of a feature or connection structure with an integrated valve structure such as that depicted in FIGS. 8 and 9 is that no dead space is created between the feature 139*a* and the valve. In other words, all of the sample material located in the feature 139*a* is subjected to substantially the same conditions during processing. This could potentially not be the case if a valve were located downstream along the connection structure 137*b* from the feature 139*a*. In such a situation, any sample material located in the volume of the connection structure between the feature 139*a* and the valve could experience different conditions during processing, not receive the same exposure to reagents or other materials in the process feature 139*a*, etc.

A valve can also be accomplished by utilizing materials for at least the cover film 120 that can be pierced by a laser. Directing a laser at a desired region or regions of the device would open such a valve. In one embodiment, loading the disk with a material that absorbs laser energy of a certain wavelength can form this type of valve. A laser emitting at least that wavelength is then directed only towards the desired areas to be "opened." In one embodiment, a substrate can be loaded with an energy absorbing material and a cover film on both the first major surface and a second major surface is not loaded. When the laser is directed towards the desired areas of the device, the substrate will give way allowing the fluid to pass into another feature without allowing it to escape from the device.

An energy absorbing material known to those of skill in the art, as appropriate, having read this specification, can be utilized. Examples include loading with carbon or other absorbing materials, such as dye molecules. In one embodiment, carbon is utilized.

For connection structures that function to transport sample from one feature to a channel for capillary electrophoresis, it may be desirable to utilize other type of valve systems. Examples of these valve systems can be found in U.S. Pat. No. 6,532,997, the disclosure of which is incorporated by reference herein.

Although particular types of valves are shown here, those skilled in the art, having read this specification, will recognize many other devices or constructions that could be substituted for the exemplary valves or constricted passage. These alternatives may include, but are not limited to, porous plugs, porous membranes, tortuous pathways, hydrophobic differences in surfaces, pneumatic or piezoelectric, or mechanically operated valves.

Capillary Electrophoresis Interface

Devices of the invention may also include injection ports configured to interface with a single capillary or a capillary array to transfer a sample or samples from the device for separation by capillary electrophoresis.

Figure 10A:
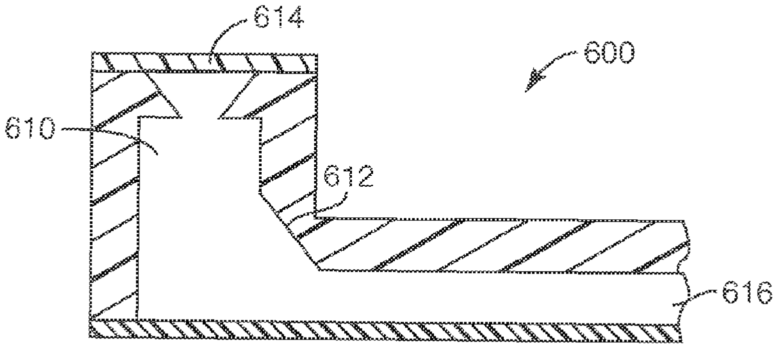
FIGS. 10*a, b*, and *c* depict various views of an exemplary capillary electrophoresis injection port configuration; (a) cross-sectional view, (b) top view and (c) bottom view.
Figure 10B:
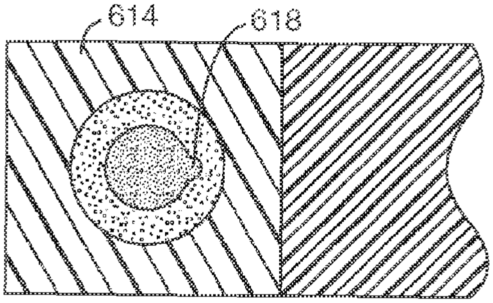
Figure 10C:
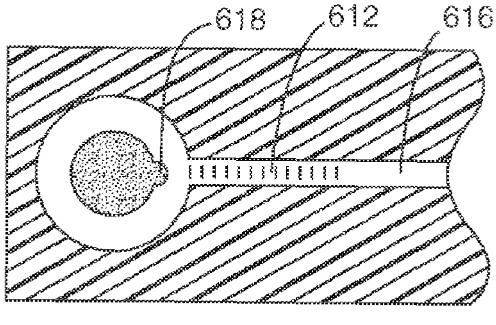

FIGS. 10*a, b*, and *c* depict an exemplary configuration of an injection port 600 which can be incorporated into the device. The injection port is designed to allow the capillary and electrode to pierce a film covering the port and make contact with the processed sample solution so that an aliquot of the solution can be removed from the device for analysis and/or further processing. The injection ports may be situated, for example, to allow access to a compartment or wall of the device, that in turn may be in contact with a compartment connection structure 616.

Figure 11:
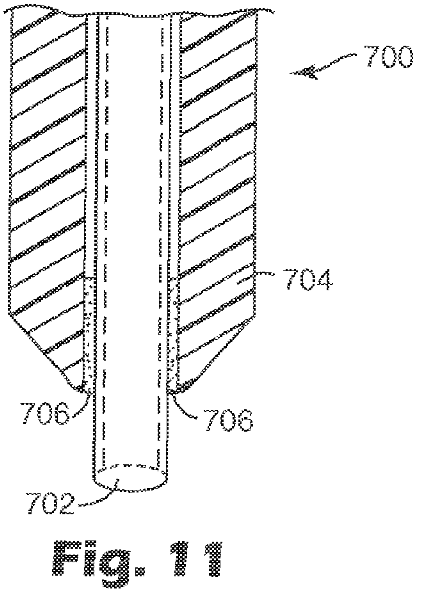
FIG. 11 depicts a cross-sectional view of an example of a capillary electrode configuration in accordance with the invention.

The capillary injection port 600 depicted in FIGS. 10*a, b*, and *c* includes a needle void 610, an angled entry channel 612 and a film 614. The needle void 610 functions to allow a sample collection needle (an example of which is depicted in FIG. 11) access to a processed sample that is contained in the device. The needle void 610 can also be designed to allow any commonly used sample collection needle to be used with a device of the invention.

The film 614 functions to seal the capillary injection port 600 until the needle void 610 is accessed. In one embodiment, the film 614 is made of the same types of film as the cover film 120 discussed earlier. In one embodiment, the film 614 and the cover film 120 are the same film, i.e., one piece of material covers the entire device. In another embodiment, the film 614 (and alternatively the cover film 120 as well) is made of a film that is capable of resealing itself once the sample needle is removed. The port 600 is designed with an angled entry channel 612 and bleed notch 618 to allow air to escape the port 600, without disturbing the solution, when the capillary and electrode pierce the film 614.

FIG. 11 depicts an exemplary sample collection needle 700. The sample collection needle 700 includes a capillary 702 and an electrode 704. In one embodiment, the capillary 702 is held in the electrode 704 through use of an adhesive 706. In one embodiment, the adhesive 706 is epoxy. The capillary 702 may extend beyond the end of the electrode 704 to avoid introduction of bubbles into the capillary during sample extraction and separation.

The capillary 702 can be pre-loaded with separation buffer before it is introduced into port 600 of the device. When the capillary and electrode have made contact with the processed sample solution, a small aliquot of the solution may be introduced into the capillary by electro-kinetic injection. After injection of the processed sample solution into the capillary, the sample collection needle is removed from the device and the film reseals. The resealing feature of the film allows the device and remaining sample solution to be archived. Further detail on this type of exemplary interface configuration and construction can be found in U.S. application Ser. No. 10/324,283 or U.S. application Ser. No. 10/339,447, the disclosure of which is incorporated herein by reference.

Integrated Electrodes

Devices of the invention can also include integrated electrodes. An integrated electrode is one that has at least a portion thereof releasably attached to the substrate. In one embodiment, a device of the invention includes an integrated electrode in connection with the unvented channel. In such an embodiment, the unvented channel can be but need not be, utilized for IEF. One advantage of an integrated electrode in instances where the unvented channel is utilized for IEF is that it allows for minimal user intervention with the electrode and/or device before the sample is transferred from the connected compartments. Minimal user intervention can minimize the time delay between the IEF separation of the sample and the transfer of the fractions, which in turn can minimize diffusion of the analyte between the pH bins of the unvented channel. Another advantage of the attached electrodes is they prevent the anolyte or catholyte from being expelled from the device during rotation.

Devices of the invention can also include integrated electrodes in connection with other features of the device. Examples of such other features include, but are not limited to, connection structures where the integrated electrode serves to determine the pH or other characteristic of a solution that is within or passing through the connection structure, and channels that can be used for capillary electrophoresis.

Figure 12A:
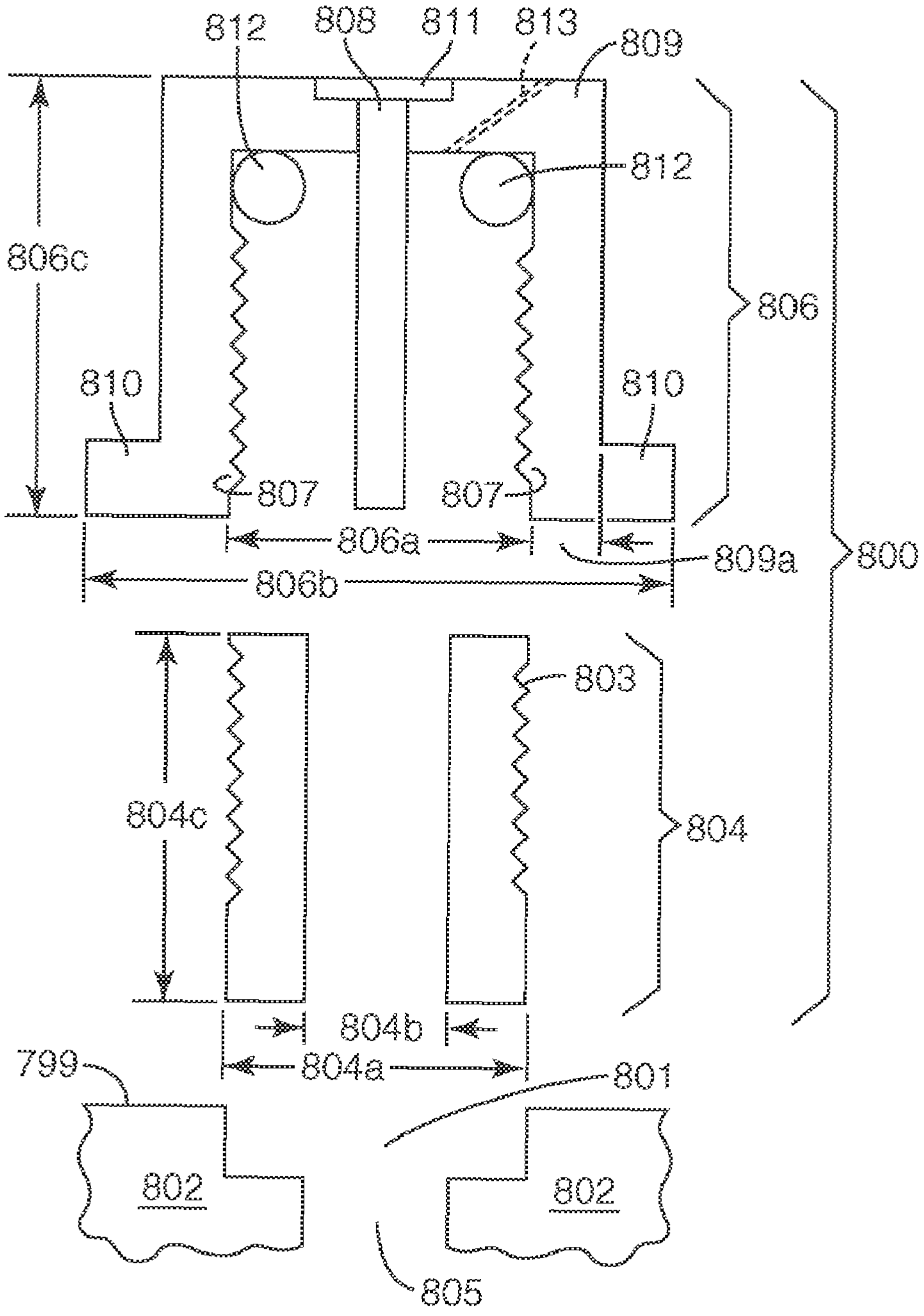
FIGS. 12*a, b*, and *c* are expanded views of an integrated electrode in accordance with the invention.

In one embodiment of the invention, the integrated electrode is releasably attached to the substrate 802 of the device through threads. An example of a cross-section of such an embodiment can be seen in FIG. 12*a*. This embodiment of an integrated electrode 800 includes a first piece 804 and a second piece 806. The first piece 804 is generally a cylinder that is open on both ends and configured to be placed in contact with the substrate 802. The first piece 804 includes threads 803 on the outside surfaces of the first piece 804.

The first piece 804 generally has an outer diameter 804*a* of about 1 mm to about 10 mm. In one embodiment, the outside diameter 804*a* of the first piece 804 is about 3 to 5 mm. In yet another embodiment, the outside diameter 804*a* of the first piece is about 4 mm. The outside diameter 804*a* of the first piece 804 also dictates the diameter of the inset 801 in the substrate 802. Below the inset 801 in the substrate 802 the space may, but need not narrow so that the first piece 804 has a ledge in the substrate 802 to rest on. It should also be understood that the substrate 802 in FIG. 12*a* continues beneath the depiction of the wavy line so that the electrically conductive portion 808 will be in connection with the sample within a feature of the device.

The inside diameter of the interior of the cylindrical first piece 804 is given by 804*b*. Generally, the inside diameter 804*b* is about 0.5 mm to about 9 mm. In one embodiment, the inside diameter 804*b* is about 1 mm to about 3 mm. In yet another embodiment, the inside diameter 804*b* is about 2 mm. The height 804*c* of the first piece 804 is dictated at least in part by the height 806*c* of the second piece 806.

The second piece 806 includes a cap 809 and an electrically conductive member 808, and can generally be described as fitting over the first piece 804. The second piece 806 has a thread on the interior side surface 807 of the cap 809 that fastens the second piece 806 into place on the first piece 804. The inside diameter 806*a* of the second piece 806 is dictated by the outside diameter 804*a* of the first piece 804. The outside diameter 806*b* of the second piece 806 is dictated at least in part by the inside diameter 806*a* and the thickness 809*a* of the cap 809. In one embodiment the cap 809 includes an extension 810 that extends outward from the main portion of the cap 809 and rest on the first major surface 799 of the substrate 802 when the integrated electrode 800 is assembled. In such an embodiment, the outside diameter 806*b* is generally about 3 mm to about 15 mm. In one embodiment, the outside diameter is about 7 to about 9 mm. In yet another embodiment, the outside diameter is about 8 mm. The height 806*c* of the second piece is dictated at least in part by the height of the first piece 804. In general, the height 806*c* of the second piece 806 is about 1 mm to about 10 mm. In one embodiment, the height of the second piece 806 is about 5 to about 7 mm. In yet another embodiment, the height of the second piece 806 is about 6 mm.

The second piece 806 also includes an electrically conductive member 808. The electrically conductive member

808 is generally in the center of the cap 809 and extends downward from the top of the cap 809 towards the base of the cap 809. The material of the electrically conductive member 808 extends through the entirety of the cap 809 so that electrical contact can be made with it on the surface of the cap 809. In one embodiment, the electrically conductive member 808 has a top 811 that has a wider diameter than the rest of the electrically conductive member 808. The function of the wider top 811 is so that it is easier to make electrical contact between the electrically conductive member 808 and a power supply (not shown). The length of the electrically conductive member may be a compromise between a longer electrically conductive member that ensures good contact with the solution and a shorter electrically conductive member that is more sturdy. In one embodiment, the electrically conductive member 808 extends to the base of the cap 809.

In one embodiment, the second piece 809 also includes an O-ring 812. The O-ring 812 functions to create a seal between 804 and 806. Generally, the size of the O-ring 812 is dictated at least in part by the overall size of the first 804 and second piece 806. In one embodiment, the O-ring 812 has an inner diameter of 2 mm and is 1 mm wide. In another embodiment, rubber, silicone gasket, or high viscosity oil can be utilized to create a seal between 804 and 806.

In one embodiment, the second piece 806 also includes an air vent 813. The air vent 813 functions to prevent disruption to the sample within the integrated electrode 800 that could result from a build up of pressure as the second piece 806 is fastened in place on the first piece 804. The air vent 813 also functions to allow the release of gases that may be formed at the electrically conductive member 808. In one embodiment, the diameter of the vent is less than 1 mm and is designed to not interfere with O-rings.

Figure 12B:
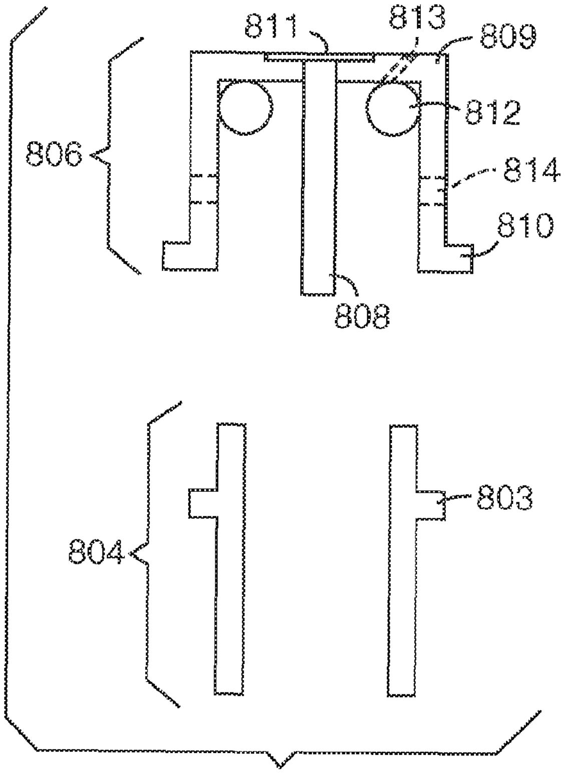
Figure 12C:
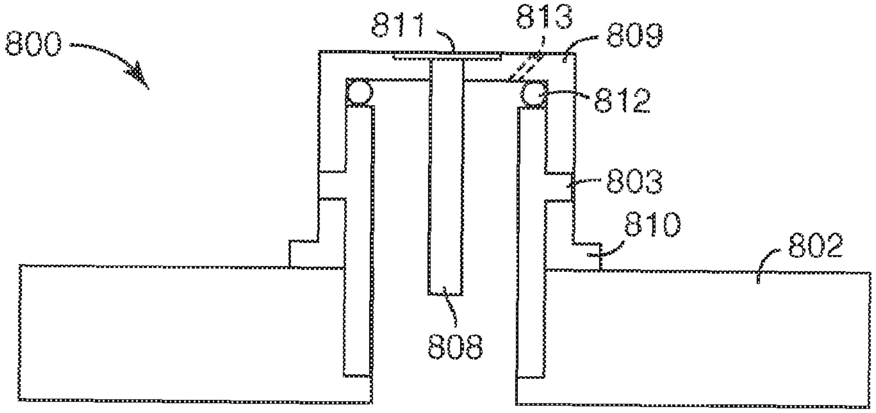

In another embodiment of the invention, the integrated electrode is releasably attached to the substrate 802 of the device through a pin and slot mechanism. An example of such an embodiment can be seen in FIG. 12*b* (cross-section view of separate components) and FIG. 12*c* (cross-section view of assembled electrode). This embodiment of an integrated electrode 800 includes a first piece 804 and a second piece 806. The first piece 804 is generally a cylinder that is open on both ends and configured to be placed in contact with the substrate 102. The first piece 804 includes pins 803 on the outside surfaces of the first piece 804 that mates with slot 814.

In one embodiment, the first piece 804 and the cap 809 of the second piece 806 are made of the same material, and in another embodiment, the first piece 804 and the cap 809 of the second piece 806 are made of different material. Any material known to those of skill in the art having read this specification, as appropriate for manufacture of the first piece 804 and the cap 809 of the second piece 806 can be utilized. Examples of such materials include, but are not limited to, polyolefins, polypropylene, polycarbonates, high-density polyethylene, polymethyl methacrylates, polystyrene, polytetrafluoroethylene (Teflon® available from Dupont), polysiloxanes, or combinations thereof. In one embodiment, the first piece 804 and the cap 809 of the second piece 806 are made polypropylene. The first piece 804 and the cap 809 of the second piece can be fabricated by any appropriate method known to those of skill in the art. Examples of which include, but are not limited to, injection molding and micro-machining for example. In one embodiment, the first piece 804 and the cap 809 are fabricated by injection molding.

The electrically conductive material 808 can be made of any material known to those of skill in the art as appropriate for manufacture of an electrode. Examples of such materials include platinum, gold, copper, or alloys. In one embodiment, the electrically conductive material 808 is made of platinum. The electrically conductive material 808 can be fabricated by any appropriate method known to those of skill in the art. Examples of such methods include, but are not limited to, wire drawing, metal casting or soldering the discrete parts. In one embodiment, the electrically conductive material 808 is fabricated by soldering a wire to the electrode plate. The electrically conductive material 808 can be fabricated within the cap 809 or it can be fabricated outside the cap 809 and placed in the cap after fabrication. In either case, the electrically conductive material 808 can be either simply placed within the cap 809 or it can be secured within the cap 809. If the electrically conductive material 808 is to be secured within the cap 809, it may be adhered thereto. Examples of adhesives that could be used for adhering the electrically conductive material 808 to the cap 809 include, but are not limited to, epoxies. In one embodiment, the electrically conductive material 808 is adhered to the cap 809 with an epoxy.

Figure 13A:
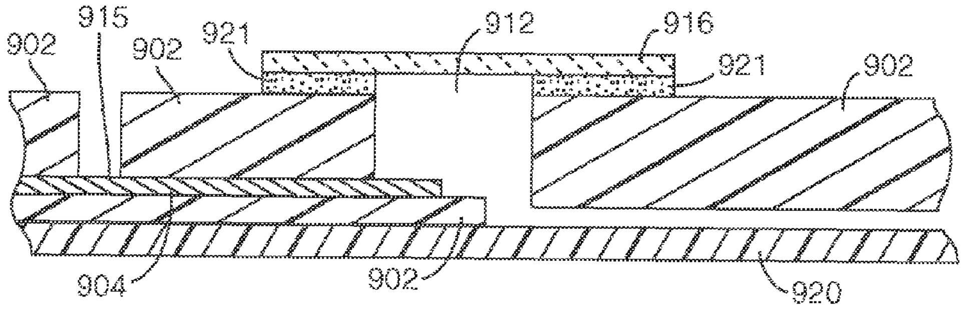
FIGS. 13*a, b*, and *c* are cross-sectional views of integrated electrodes in accordance with the invention.

In one embodiment of the invention, the integrated electrode is attached to the substrate 902 of the device. An example of such an embodiment can be seen in FIG. 13*a*. This embodiment of an integrated electrode 904 includes an electrode incorporated into the device. Contact with the electrode 904 can be achieved at contact points 915 which are either at the edge of the device, from the top side of the device or from the side of the device. One end of the electrode 904 is configured to make contact with the solution in the electrode well 912.

The electrode well 912 can be covered with a porous material 916 after the well 912 has been filled with solution. The porous material 916 is attached to the device by an adhesive 921. The porous material 916 serves to allow the escape of the electrolytic gases formed in the well 912 by electrolysis of the water. The porous material 916 also prevents the solution being expelled from the device during rotation. Generally, the porous material 916 is hydrophobic. Examples of such materials include but are not limited to membranes, non-wovens, and ceramics. In one embodiment, the porous material 916 is made of polypropylene manufactured by the thermally induced phase separation (TIPS) process.

Figure 13B:
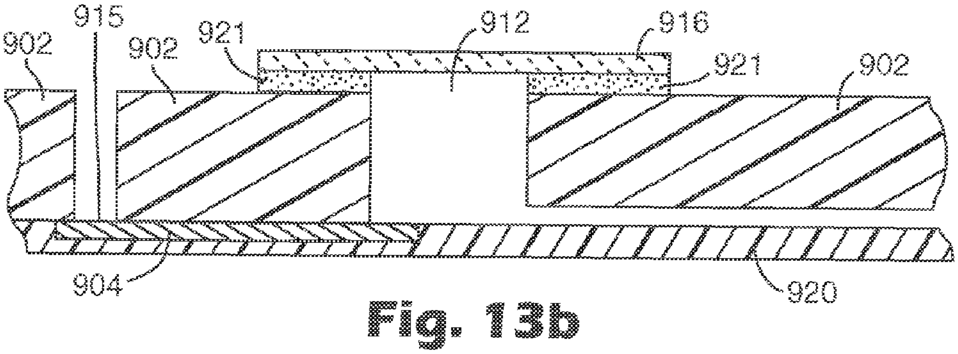

In one embodiment of the invention, the integrated electrode 904 is deposited to the cover film 920 of the device. An example of such an embodiment can be seen in FIG. 13*b*. Contact with the electrode 904 can be achieved at the contact point 915, which is at the top side of the device. The one end of the electrode 904 is configured to make contact with the solution in the electrode well 912.

Figure 13C:
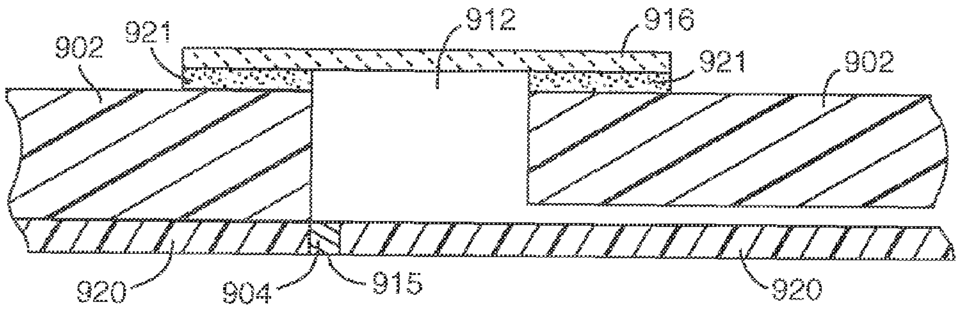

Another embodiment of an integrated electrode is seen in FIG. 13*c*. This embodiment allows contact to be made through the bottom of the device, the electrode 904 would be formed by enclosing a through hole in the cover film 920 with electrode material. This would then provide a means for electrical continuity from the device platform to the device.

The electrode 904 is generally made of a thin film of a conducting material, such as platinum, gold, copper or an alloy for example. In one embodiment the electrode 904 is gold. The electrically conducting trace can be formed by vapor deposition, vacuum deposition, metal sputtering, printing of conducting material (inks) or any other method known to those of skill in the art, having read this specification. In one embodiment, the electrode is manufactured vapor deposition.

Figure 14:
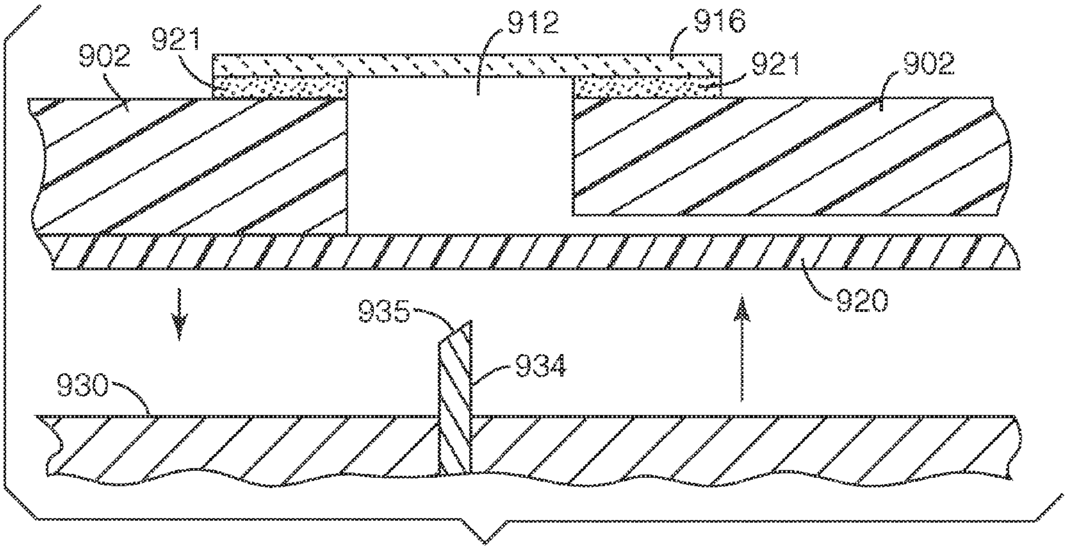
FIG. 14 is a cross-sectional view of an electrode that is integrated into the base on which the device rotates.

In one embodiment of the invention, the electrode is integrated into the rotating platform on which the device can be used. An example of such an embodiment can be seen in FIG. 14. Contact with the electrode 934 can be achieved through the platform 930 on which the device can be rotated. In one embodiment, the platform 930 has a mercury junction point that maintains a current flow in the rotating system. Contact can also be made through the under side of the platform. In the electrode configuration where contact is made through the bottom of the device, the upper end 935 of the electrode 934 is configured to make contact with the solution in the electrode well 912.

The electrode 934 can be a thin wire, such as platinum, gold, copper or an alloy. In one embodiment the electrode 934 is platinum. The electrode 934 can also be a pin that may pierce the cover film 920 that is adhered to the device. When the device is removed from the platform 930 the cover film 120 can reseal, preventing the solution from exiting the disk.

Control Systems for Devices of the Invention

Devices of the invention can be used in connection with systems to control the device and the conditions in which the device exists. Examples of such systems include but are not limited to, a personal computer (pc) controlled base to control rotation of the device, a cooling system to cool the entire device or selected portions thereof, a heating system to heat the entire device or selected portions thereof, a laser system for opening the valves and an electrode contact/connection system.

One example of a system that can be used to control the device is a pc controlled base to control the rotation of the device. In one embodiment, a pc is used to control the rotation of a brushless electrical motor through an external driver and the optical encoder on the motor. The platform that interfaces with the disk is connected to the drive shaft of the motor. The position, speed, acceleration and time of motion for the motor and, therefore, disk is controlled by the pc.

One example of a cooling system to cool the entire device or selected portions thereof includes a ring made of a material with a high thermal conductivity in connection with the pc controlled base. Examples of such materials include but are not limited to aluminum, copper and gold. In one embodiment the aluminum ring, for example, can be configured to underlie the entirety of the device, and in another embodiment, the aluminum ring can be configured to underlie only a portion of the device. In an embodiment of the invention where the unvented channel is utilized for IEF, the aluminum ring is generally configured to at least underlie the unvented channel. Such a configuration serves to reduce the effects of Joule heating. The aluminum ring cools the portion of the device that it is in contact with, by being cooled itself, and then absorbing heat from the device. One method of cooling the aluminum ring includes blowing cooled air on the ring. Cooling may also be performed by using gases other than air and peltier cooling systems.

One example of a heating system to heat the entire device or selected portions thereof include those found in WO 02/00347, the disclosure of which is incorporated by reference.

In one embodiment of the invention, a mechanical system can also be used to control the electrode contact/connection system. The electrode connection system provides a potential to the device, either to the top surface or the bottom surface of the device. Interfacing to the top surface, the power supply electrodes can be mechanically lowered to make contact with the integrated electrodes on the top surface of the device. At the completion of the experiment, the electrodes can be mechanically raised. The power supply electrodes can be interfaced with the device through the rotation platform. The power is supplied to the platform through a mercury junction between the platform and the motor. The platform features electrodes that make direct contact with the device. Examples of the integrated electrode configurations have been previously described.

Methods of Using a Device of the Invention

The particular methods of using a device of the invention are dictated at least in part by the particular application that the device is configured for.

In an embodiment where the device is configured for IEF of a protein sample, one exemplary method of using a device of the invention is as follows. The protein sample, is loaded into the first sample well of the unvented channel. The sample is then allowed or forced into the IEF channel until it reaches the other well. The anolyte solution is then added in one of the wells and in the other well the catholyte solution is added. After the samples and solutions are loaded, the electrodes (the anode with the anolyte and the cathode with the catholyte) are contacted with the solution in the sample wells. Alternatively, the device can be placed on the platform and loaded with sample as described. The anolyte is loaded into the anode well and the catholyte is loaded into the cathode well. The wells are then covered with a porous membrane and held in place by adhesive. A power supply is then hooked up to the electrodes and a voltage is applied. The voltage is applied until the current decreases and reaches a steady state value. Then the device is rotated to transfer the protein fractions from the connected compartments of the unvented channel through the plurality of compartment connection structures to the plurality of chambers. The protein fractions in the chambers can then be further analyzed by any technique known to those of skill in the art to be applicable to protein fractions.

In an embodiment where the device includes an integrated electrode, the step of contacting the electrodes with the solution would include fastening the second piece of the integrated electrode onto the first piece of the integrated electrode ensuring that the electrically conductive material contacted the solution within the sample well.

In an embodiment where the device is configured for IEF of a protein sample and subsequent processing, an exemplary method includes the steps above for a method of IEF followed by those given below. Once the proteins fractions are in the chambers, the subsequent processing can be undertaken. If the subsequent processing is denaturation of the proteins, the plurality of chambers, which can be prefilled with reagents are heated. The denatured proteins can then be taken from the device to perform further analysis.

In another embodiment, the proteins can be labeled at the same time that they are denatured to facilitate subsequent detection. In such an embodiment, the steps are the same as discussed above, except that the reagents contained in the chamber included labeling reagents as well as denaturing reagents.

In yet another embodiment, analysis subsequent to protein denaturation and labeling, such as capillary electrophoresis, can also be carried out on a device of the invention. After the proteins are denatured and labeled, the valves in the plurality of chamber connection structures are opened. The device is then rotated to transfer the denatured, labeled proteins to the capillary electrophoresis channels. Electrodes are then connected with the capillary electrophoresis channel and the power supply. The separated proteins can then be detected using laser-induced fluorescence.

In a further embodiment, the proteins that were separated by capillary electrophoresis can be further analyzed by mass spectroscopy.

In another embodiment, the samples that have been separated by IEF in the unvented channel can be subject to trypsinization in a chamber or bin. Alternatively, the digested samples can also be desalted. One of skill in the art, having read the specification, would know the steps, reaction conditions, and reagents necessary to carry out these steps.

In another embodiment, the samples can be removed from the device at any point and transferred to undertake other analysis, such as capillary electrophoresis (off-device) liquid chromatography, polyacrylamide gel electrophoresis, and mass spectroscopy for example. The device of the invention may, but need not be configured for automated transfer of the samples.

One embodiment of the invention includes a method of performing isoelectric focusing of a protein sample that includes loading a sample containing protein into the first sample well of a device of the invention, allowing or forcing the sample into the unvented channel until it reaches the second sample well, adding anolyte solution into the first sample well, adding catholyte solution into a second sample well, contacting the integrated electrodes of the device with the solution in the sample wells, and applying a voltage to the electrodes. Alternatively, the first and second sample wells can be covered with a porous membrane before or after the voltage is applied to the electrodes.

Another embodiment of the invention includes a method of performing isoelectric focusing of a protein sample that includes loading a sample containing protein into the first sample well of a device of the invention, allowing or forcing the sample into the unvented channel until it reaches the second sample well, adding anolyte solution into the first sample well, adding catholyte solution into a second sample well, contacting the integrated electrodes of the device with the solution in the sample wells, applying a voltage to the electrodes, covering the first and second sample wells (either before or after the voltage is applied to the electrodes) with a porous membrane, and rotating the device to transfer the protein fractions from the connected compartments of the unvented channel to the chambers. The device can be rotated at speeds and for amounts of time as discussed above.

Another embodiment of the invention includes a method for performing isoelectric focusing on a sample and subsequently processing the fractioned samples that includes loading a sample containing protein into the first sample well of a device of the invention, allowing or forcing the sample into the unvented channel until it reaches the second sample well, adding anolyte solution into the first sample well, adding catholyte solution into a second sample well, contacting the integrated electrodes of the device with the solution in the sample wells, applying a voltage to the electrodes, covering the first and second sample wells (either before or after the voltage is applied to the electrodes) with a porous membrane, rotating the device to transfer the protein fractions from the connected compartments of the unvented channel to the chambers, and heating the chambers, which are prefilled with reagents capable of denaturing proteins to denature the proteins. A further embodiment includes labeling the proteins in the same or a different chamber in which they are being denatured. Alternatively, the proteins can be subjected to trypsinization in the first chamber or a subsequent chamber. Protein samples that have been subject to trypsinization can also subsequently be desalted.

Another embodiment includes a method for performing isoelectric focusing, processing and capillary electrophoresis of a sample containing protein that includes loading a sample containing protein into the first sample well of a device of the invention, allowing or forcing the sample into the unvented channel until it reaches the second sample well, adding anolyte solution into the first sample well, adding catholyte solution into a second sample well, contacting the integrated electrodes of the device with the solution in the sample wells, applying a voltage to the electrodes, covering the first and second sample wells (either before or after the voltage is applied to the electrodes) with a porous membrane, rotating the device to transfer the protein fractions from the connected compartments of the unvented channel to the chambers, and reacting the protein fractions in the chambers to denature and label them, opening the valves in the chamber connection structures in the device, rotating the device to transfer the denatured, labeled proteins to a capillary electrophoresis channel, and connecting electrodes to the capillary electrophoresis channel electrodes and the power supply. Denatured and labeled protein fractions that are separated by capillary electrophoresis can be detected using a number of techniques, including laser-induced fluorescence or mass spectroscopy.

Any of the above methods, or others envisioned for using a device of the invention, can be modified according to the knowledge of one of skill in the art, having read this specification, for example, samples can be removed at any time during the processing to undertake other off-device analysis such as for example, capillary electrophoresis (off-device), liquid chromatography, polyacrylamide gel electrophoresis, and mass spectroscopy. One of skill in the art, having read this specification, will also understand that virtually any combination of device features discussed above with respect to the device can be utilized in methods of the invention. One of skill in the art will also understand, having read this specification, that a number of the reagents or solutions can be loaded into a device of the invention before the ultimate user obtains the device, and one of skill in the art would understand that this would modify the method steps accordingly.

EXAMPLES

All chemicals were obtained from Aldrich (Milwaukee, Wis.) and were used without further purification unless indicated otherwise.

Example 1

Comparison of IEF Separation with a Device of the Invention Including an Integrated Electrode and a Commercially Available System A device, in accordance with the invention, configured to perform IEF, was fabricated and compared with a standard system.

Figure 15:
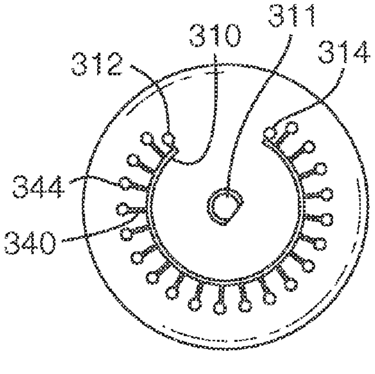
FIG. 15 is a plan view of a device for iso-electric focusing in accordance with the invention.

The substrate was fabricated from polypropylene and sealed on the first major surface with a cover film made of polyolefin with a pressure sensitive adhesive. The configuration of the device can be seen in FIG. 15. In FIG. 15, 311 represents the hub for rotation around a central axis, 310 represents the unvented channel configured for IEF, 312 represents the first sample well, 314 represents the second sample well, 340 represents one of the plurality of compartment connection structures, and 344 represents one of the plurality of chambers.

The unvented channel for IEF is approximately 100 mm in arc length, and has 20 connected compartments. The angles of the leading and trailing edges in the connected compartments are about 10°. The volume of the connected compartments was approximately 5 μl. The leading edge and trailing edge angles of the connected compartments are thought to minimize fluid inertia in the unvented channel.

The device was placed on a base configured to rotate the device and was controlled by a PC. Cooling capabilities were added to the base to reduce the temperature effects associated with Joule heating. Temperature controlled air was introduced via an airline and directed at the underside of the device to an aluminum ring. The device and base were configured so that the aluminum ring was positioned directly below the unvented channel.

The device also contained an integrated electrode. The first piece snapped into and was pressure fitted into one of the sample wells and served as a fluid reservoir. The first piece had threads on the outside of the piece, to which the second part was fastened into place. The second piece contained Pt as the electrically conductive material in the center of the piece and covered the sample reservoirs. The Pt extended through the cap to a conducting touch pad. Electrical contact was made to the solution from the power supply through the touch pad and Pt. The cap also had a vent to prevent disruption to the fluid in the well that would result from a build up of pressure as the cap is fastened in place.

A 4 protein sample of cytochrome C, myoglobin, human serum albumin (HSA), and phycocyanin (Sigma, St. Louis, Mo.) was solubilized in a 2.5% BioRad 3-10 Ampholyte (pH 3-10) (Catalog #163-1113) (Bio-Rad, Hercules, Calif.), 20 mM octyl glucopyranoside (OGP) (Alexis Corporation, Lausen, Switzerland), 6.0 M urea solution and deionized $H_2O$ to give a solution with a final concentration of 4 mg/ml for each protein. The anolyte was 0.3 M $H_3PO_4$ and the catholyte was 0.3 M NaOH.

The ampholyte molecules were acrylamide oligomers with side groups of different $pK_a$ values and, in solution formed the pH gradient between the anolyte and the catholyte. The unvented channel was carefully filled with the protein-ampholyte sample solution, ensuring no bubbles were formed. The first (anode) sample well was filled with the low pH anolyte solution and the second (cathode) sample well was filled with the high pH catholyte solution.

The integrated electrodes were then fastened in the sample wells, ensuring contact between the Pt and the solution. Electrodes from the high voltage power supply are then placed in contact with the Pt electrode touch pads. The voltage was applied, and the current and temperature arising from Joule heating were monitored. The electric field strength used was 200 V/cm. The current decreases during the focusing of the protein samples due to the reduced number of charged moieties in solution. The current was observed to reach a steady state value when the IEF of the proteins was complete. The time the IEF equipment generally takes to reach steady state is dependent on each protein's electrophoretic mobility, which in-turn is dependent on the temperature, solution viscosity and electric field strength. In this example, the electric field was applied to the solution for approximately 45 minutes.

After the IEF of the proteins, the device on the platform was rotated at 5000 rpm for about 10 seconds at an acceleration of about 100 rad.s$^{-2}$. The centrifugal force ensures uniform pressure on the solution in the channel and therefore, uniform fluidic transfer from the IEF bins at the same radius. The diffusion between the adjacent pH bins, defined by the compartments in the unvented channel was minimized by the serrated design of the unvented channel.

Figure 16A:
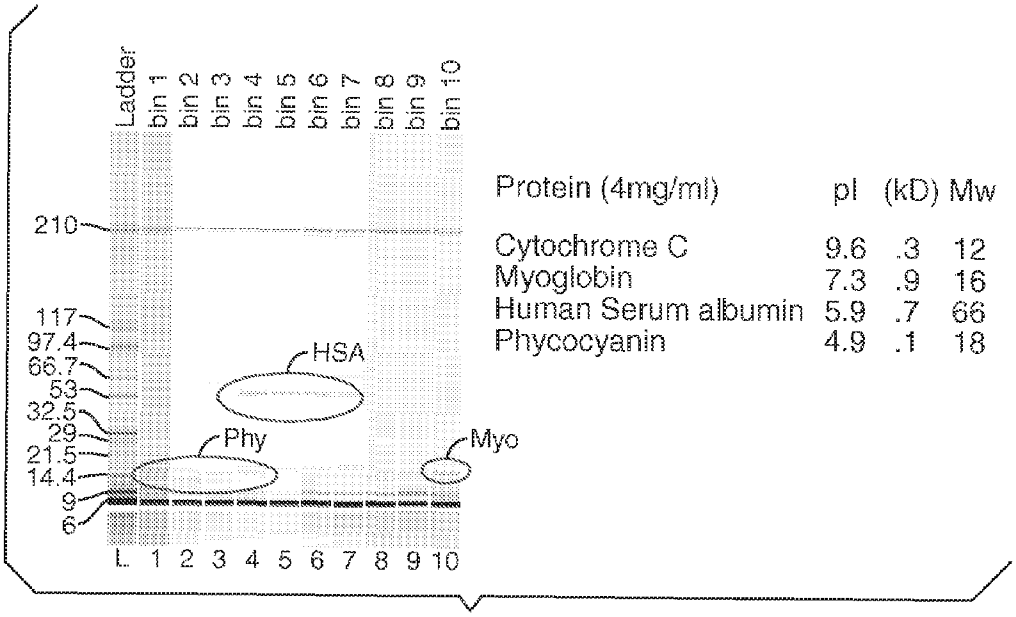
FIGS. 16*a*, and *b* depict a two-dimensional virtual gel obtained from protein fractions obtained from a device for iso-electric focusing.
Figure 16B:
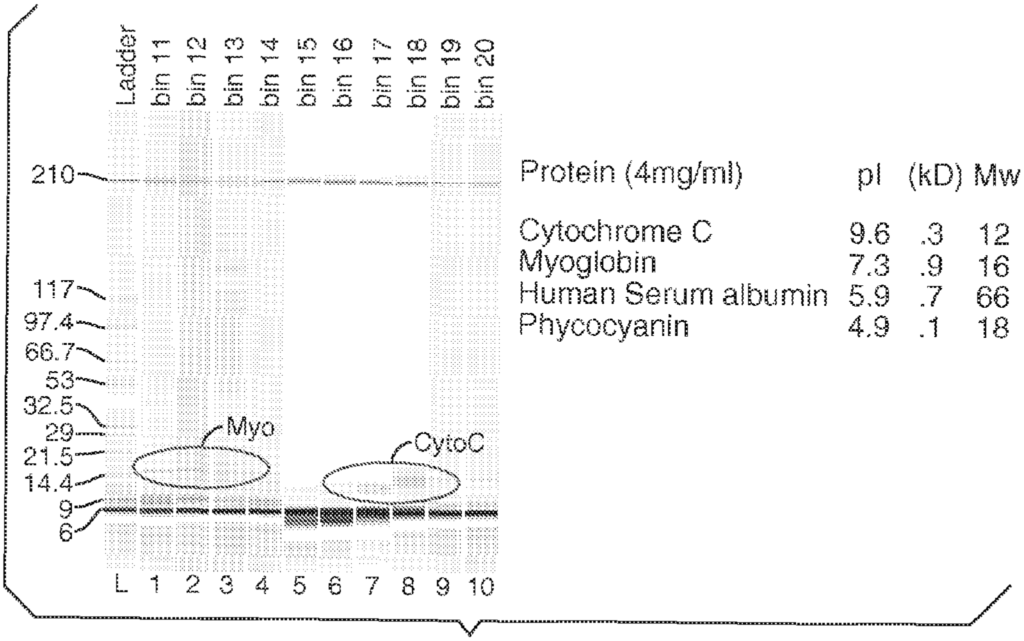

An Agilent 2100 Bioanalyzer (Agilent Technologies, Palo Alto, Calif.) was used to perform the molecular weight separation on the protein samples from the pH bins. After centrifugation of the device, the twenty protein fractions were collected and prepared for analysis by the Agilent Bioanalyzer following the standard protocol. The twenty fractions were placed into the corresponding sample wells on two Bioanalyzer Labchips (Agilent Technologies, Palo Alto, Calif.), which were then individually loaded and run on the analysis unit. Electropherograms were collected for each protein fraction. FIGS. 16*a* and *b* show images produced by transformation of the electropherograms using the Agilent Bioanalyzer software. The first lanes represent the standard protein ladder used to calibrate the apparatus and the following lanes represented the 20 protein fractions, increasing in pH. The theoretical protein pI and $M_w$, shown in Table 1 below, were used to assign the proteins in the virtual two-dimensional gel image of the 4-protein standard.

TABLE 1

| Protein (4 mg/mL) | pI | $M_w$ (kD) |
|---|---|---|
| Cytochrome C | 9.6 | 12.3 |
| Myoglobin | 7.3 | 16.9 |
| Human serum albumin | 5.9 | 66.7 |
| Phycocyanin | 4.9 | 18.1 |

For comparison purposes, the protein compositions of the twenty bins were directly compared to the output from the BioRad Rotofor™ (Bio-Rad, Hercules, Calif.) system. The BioRad Rotofor™ is a commercially available apparatus that is used to perform larger scale IEF of complex protein mixtures. In these experiments, the protein samples, anolyte, and catholyte solutions are prepared as previously described.

0.4 mg each (100 μL) of phycocyanin, HSA, myoglobin, and cytochrome C were loaded along with 380 μL of Bio-Rad's ampholyte 3-10 (2.0%) and 95 μL Serva's ampholyte 9-11 (0.5%) (Serva, Heidelberg, Germany). The solution was brought to 19 mL with 8.0 M urea containing 0.1% OGP. The electrolytes were 0.3 M NaOH and $H_3PO_4$. The Rotofor ran for 4 hours and the voltage reached a plateau level at 3000 V after about 3 hours. Fractions were harvested, and pH and volume were measured immediately. Equal amounts of solution were taken from each fraction for SDS-PAGE analysis.

Figure 17A:
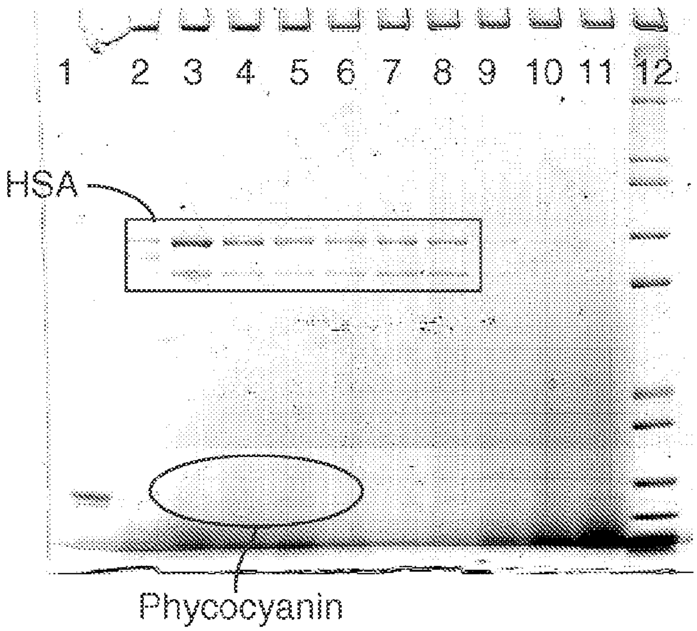
FIGS. 17*a* and *b* are a Coomassie-stained SDS-PAGE image of a protein sample using a Rotofor™ apparatus.
Figure 17B:
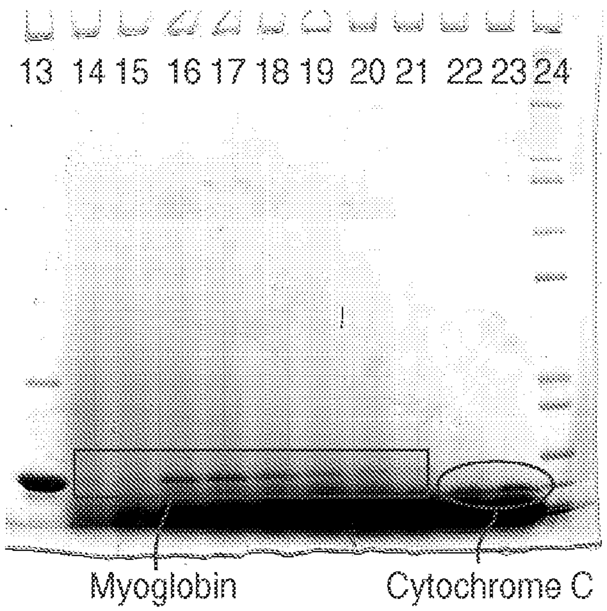

The gel image in FIGS. 17*a* and *b* represents 20 fractions from the Rotofor run where a fixed amount of sample was taken from each of the twenty fractions and run on an SDS-PAGE gel, then stained with Coomassie Blue (Bio-Rad, Hercules, Calif. Phycocyanin is known to split into three bands when separated on gels, while myoglobin into two bands, as shown here. The complex nature of HSA means that apart from forming a "thick" band, there is usually another band right below it. The gel image indicates that these four proteins are being separated according to their iso-electric points. Details of the twenty fractions can be seen in Table 2 below.

TABLE 2

| Lane Number | Fraction Number | pH | Volume (μL) |
|---|---|---|---|
| 1 | 1 μg phycocyanin | — | — |
| 2 | 1 | 3.8 | 1000 |
| 3 | 2 | 4.3 | 600 |
| 4 | 3 | 4.7 | 500 |
| 5 | 4 | 5.0 | 600 |
| 6 | 5 | 5.3 | 400 |
| 7 | 6 | 5.1 | 500 |
| 8 | 7 | 5.4 | 600 |
| 9 | 8 | 5.9 | 500 |
| 10 | 9 | 6.4 | 500 |
| 11 | 10 | 6.7 | 500 |
| 12 | Marker | — | — |
| 13 | 4 μg myoglobin | — | — |
| 14 | 11 | 6.9 | 500 |
| 15 | 12 | 7.1 | 450 |
| 16 | 13 | 7.4 | 450 |
| 17 | 14 | 7.6 | 450 |
| 18 | 15 | 7.8 | 450 |
| 19 | 16 | 8.1 | 450 |
| 20 | 17 | 8.5 | 650 |
| 21 | 18 | 9.4 | 750 |
| 22 | 19 | 10.1 | 1000 |
| 23 | 20 | 10.6 | 1000 |
| 24 | Marker | — | — |

Comparison of the protein composition between the Protein Separation System and the BioRad Rotofor™ is shown below in Table 3. As seen there, the separations are comparable. Overall, both systems produce analogous separation of the four protein sample by comparison to the gel images and protein locations.

TABLE 3

| | pI | Device Separation | BioRad Rotofor ™ |
|---|---|---|---|
| Phycocyanin | 4.9 | 1–4 | 1–4 |
| Human Serum Albumin | 5.9 | 4–7 | 1–7 |
| Myoglobin | 7.3 | 10–14 | 11–17 |
| Cytochrome C | 9.6 | 17–18 | 18–20 |

Example 2

Use of a Device of the Invention for Protein Denaturation and Off-Device Capillary Electrophoresis A device, in accordance with the invention, configured to perform iso-electric focusing, subsequent protein denaturation, and interface with capillary electrophoresis was fabricated and the feasibility of denaturing proteins in the device was investigated.

Figure 18:
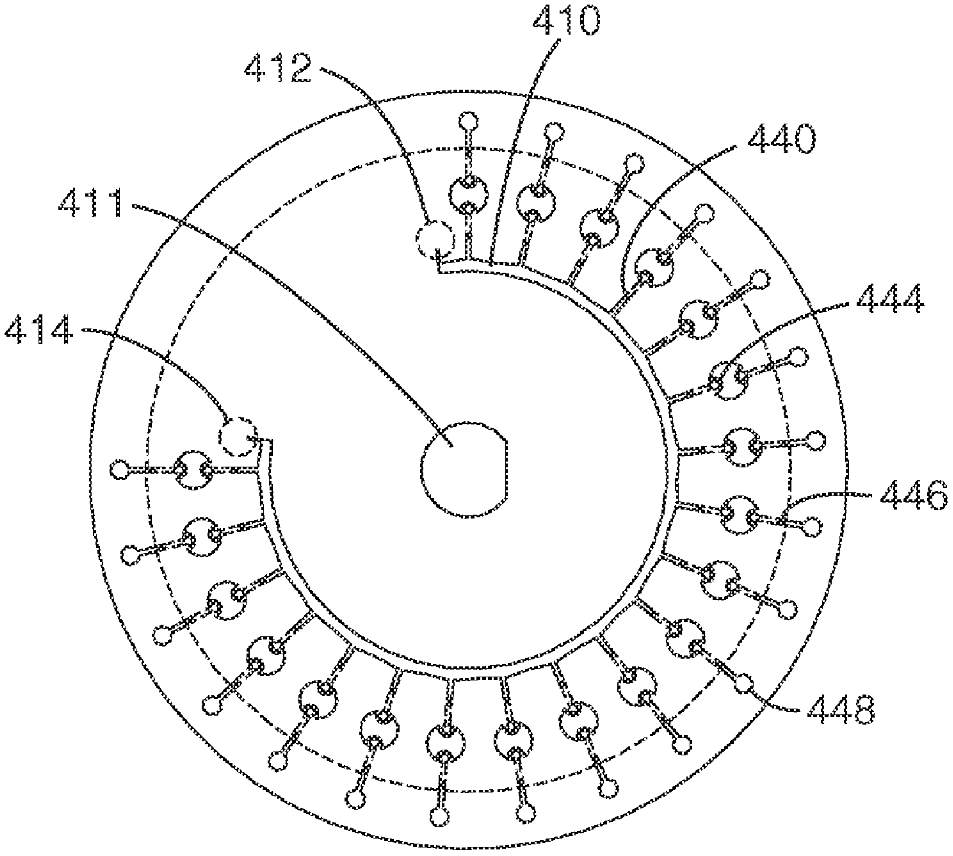
FIG. 18 is a plan view of a device for protein IEF, denaturation and capillary electrophoresis injection in accordance with the invention.

The substrate was fabricated from polypropylene and sealed on the first major surface with a cover film made of polyolefin with a pressure sensitive adhesive. The configuration of the device can be seen in FIG. 18. In FIG. 18, 411 represents the hub for rotation around a central axis, 410 represents the unvented channel configured for iso-electric focusing, 412 represents the first sample well, 414 represents the second sample well, 440 represents one of the plurality of compartment connection structures, 444 represents one of the plurality of denaturing chambers, 446 represents one of a plurality of denaturing chamber connection structures, and 448 represents one of a plurality of collection chambers.

The denaturing chambers included valves to control the flow of fluids both from the compartment connection structure to the denaturing chamber and from the denaturation chamber to the denaturation chamber connection structure. These valves are operated by impinging laser energy onto the device. The laser energy is absorbed by the carbon loaded cover film and substrate of the device to allow the fluid to pass from the volume that contains it to the next connected volume.

The device was configured for heating by the method disclosed in U.S. Pat. No. 6,532,997.

The three-protein sample (cytochrome c, β-lactoglobulin, amyloglucosidase) was solubilized in 20 mM octyl glycopyranoside solution to give a final concentration of 2 mg/mL for each protein. The octyl glycopyranoside is a non-denaturing surfactant that assists in the protein dissolution while maintaining the proteins native charge.

The sample preparation buffer from the Agilent 2100 Bioanalyzer was used as the denaturing solution. The buffer contained sodium dodecyl sulfate, lithium dodecyl sulfate and dithiothreitol. The solution also contained the lower and upper markers used for aligning and analysis of the sample electropherogram.

The three-protein sample was combined with the denaturing chemistry and subject to three different conditions. The first sample was held at room temperature for 5 minutes in a centrifuge tube, the second sample was heated to 95° C. for 5 minutes in a centrifuge tube (Standard protocol), and the third sample was heated to 95° C. in the denaturing chamber of the above described device.

The samples were collected and analyzed using the Agilent 2100 Bioanalyzer to measure the amount of denatured protein. The extent of the protein denaturing was determined by the intensity of fluorescence from the protein peak. A protein sample that has been completely denatured will afford a sharp, intense peak, while poorly denatured samples lead to relatively smaller, broad peaks. The results from the sample analysis are given in FIGS. 19*a, b*, and *c*.

Figures 19A, 19B, 19C:
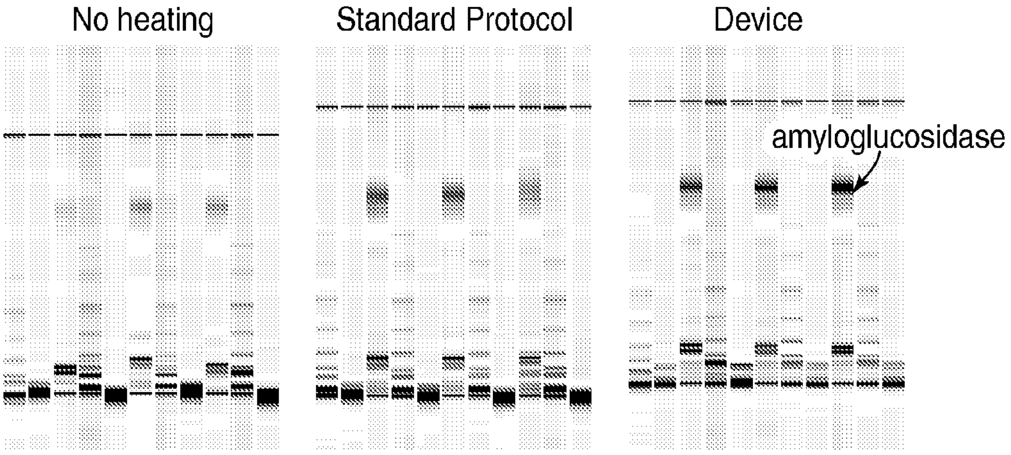
FIGS. 19*a, b*, and *c* are one-dimensional gels of a denatured protein sample that was denatured in a test tube without heating (a), in a test tube heated to 95° C. for 5 minutes (b) and in a device of the invention heated to 95° C. for 5 minutes (c).

Each gel in FIG. 19 includes the standard protein ladder (lanes 1, 4, 7, 10), denaturing solution (lanes 2, 5, 8, 11) and the three-protein solution (lanes 3, 6, 9). FIG. 19*a* is the gel of the samples held at room temperature for 5 minutes, FIG. 19*b* the gel of the samples at 95° C. for 5 minutes, and FIG. 19*c* the gel of the samples at 95° C. on the device described above for 5 minutes.

As shown by the images of FIGS. 19*a, b*, and *c*, it is possible to use the device of the invention and heating technology to denature a protein sample. The relative intensity of the amylogulcosidase peak for the standard protocol and use of the device of the invention are equivalent, and significantly greater than the peak from the room temperature conditions.

Figure 20:
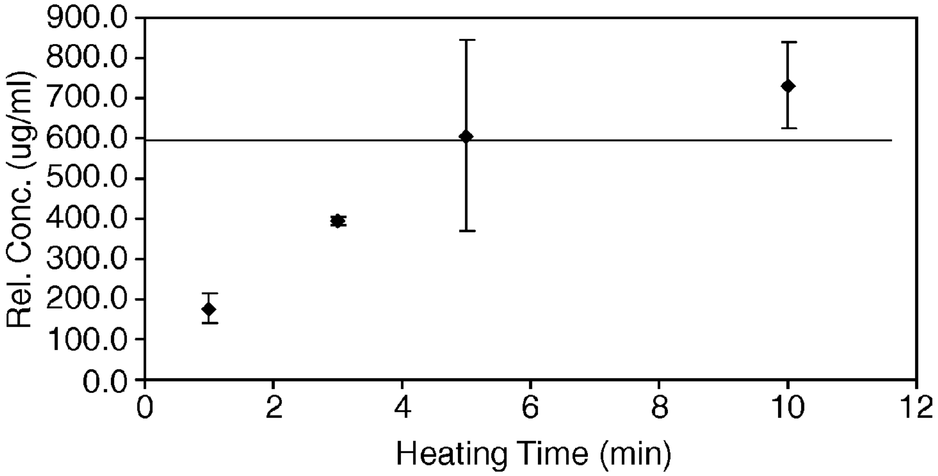
FIG. 20 is a graph showing a comparison between the relative concentration of denatured amyloglucosidase using a device of the invention that were heated for differing amounts of time.

FIG. 20 shows the relative concentration of the denatured amyloglucosidase from the device and from the standard protocol. The amount of protein recovered from the device is equivalent to the standard protocol. This experiment demonstrates the feasibility of the device to prepare a protein sample for size separation by capillary electrophoresis.

Figure 21:
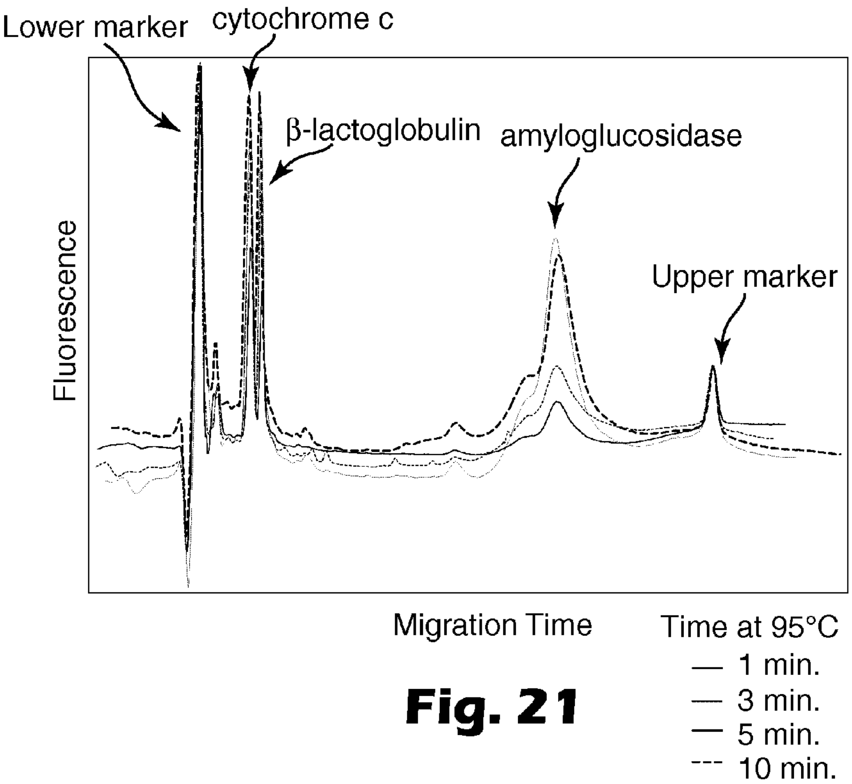
FIG. 21 shows electropherograms (fluorescence versus migration time) for proteins denatured using a device of the invention that were heated for differing amounts of time.

The same conditions as above were used to determine the time required for complete protein denaturing. Four separate protein samples were loaded into the denaturing chamber of the device and heated for 1, 3, 5, and 10 minutes at 95° C. Electropherograms (fluorescence versus migration) for the four samples can be seen in FIG. 21. As can be seen there, the protein was completely denatured after 5 minutes, and heating the sample for additional time did not increase the amount of denatured protein.

Example 3

Use of a Device of the Invention for IEF Separation and Off-Device Capillary Electrophoresis and MS Analysis A device, in accordance with the invention, configured to perform IEF, and interface with off-device capillary electrophoresis was fabricated.

The substrate was fabricated from polypropylene and sealed on the first major surface with a cover film made of polyolefin with a pressure sensitive adhesive.

The device was placed on a base that was configured for pc control of the rotational speed, and for control of cooling as discussed in Example 1 above.

The 5-protein sample (cytochrome C, myoglobin, ubiquitin, human serum albumin, and phyocyanin) was solubilized in a 3% Bio-Rad Ampholytes (Catalog #163-1113) and 20 mM octyl gluco-pyranoside solution (to give a final concentration of 4 mg/mL of each protein). 50 μL of a 12% Biolyte 3-10 ampholytes, and 2polyethylene oxide (PEO, 2% wt) were added to 150 μL of the protein stock solution to give the final protein test solution. PEO was also used to minimize non-specific binding of the proteins and control electro-osmotic flow by associating with the microchannel surface. As a consequence of the latter, entrainment into the IEF channel of the bubbles produced by electrolysis at the electrodes was minimized. The anolyte and catholyte were 0.02 M $H_3PO_4$ and 0.04 M NaOH respectively.

The IEF of the protein sample was preformed in the innermost circular saw-tooth channel of the device. The ampholyte molecules are acrylamide oligomers with side groups of different $pK_a$ values, which in solution form the pH gradient between the anolyte and catholyte. The channel was carefully filled with the protein-ampholyte sample solution, ensuring no bubbles were formed. The anode sample well (first sample well) was filled with the high pH catholyte solution. The Pt electrodes are then placed in the sample wells, ensuring contact with the solution.

The voltage was then applied and the current and temperature arising from Joule heating were monitored. The temperature and current traces can be seen in FIG. 19. The electric field strength used was about 100 V/cm. The current decreased during the iso-electric focusing of the protein samples due to the reduced number of charged species in solution carrying the electric charge. The current was observed to reach a steady state value when the IEF of the proteins was complete. The time the IEF experiment takes to reach steady state is dependent on the electrophoretic mobilities of the proteins, which in turn is dependent on the solution viscosity and electric field strength. In this example, the electric field was applied to the solution for 30 minutes.

After the proteins were iso-electrically focused, the protein samples within the individual bins were transported to the collection chambers by centrifugal transport. The separation device was placed on the base that controls the disk's position and speed of rotation. The device was spun at 5000 rpm for 10 seconds, with an acceleration of 100 $rad.s^{-2}$, to transport the samples from the IEF channel bins to the collection chambers. Centrifugal force ensures uniform pressure heads and, therefore, uniform fluidic transfer from the IEF bins on the same radius. The diffusion between the adjacent pH bins is minimized by the serrated design of the unvented channel.

An Agilent 2100 Bioanalyzer was used to execute the molecular weight separation of the protein samples. After centrifugation of the disk, the ten protein fractions were collected and prepared for analysis following the standard protocol as provided by Agilent. The ten fractions were placed into the corresponding sample wells on the Bioanalyzer Labchip, which was then loaded into the analysis unit.

Figure 22:
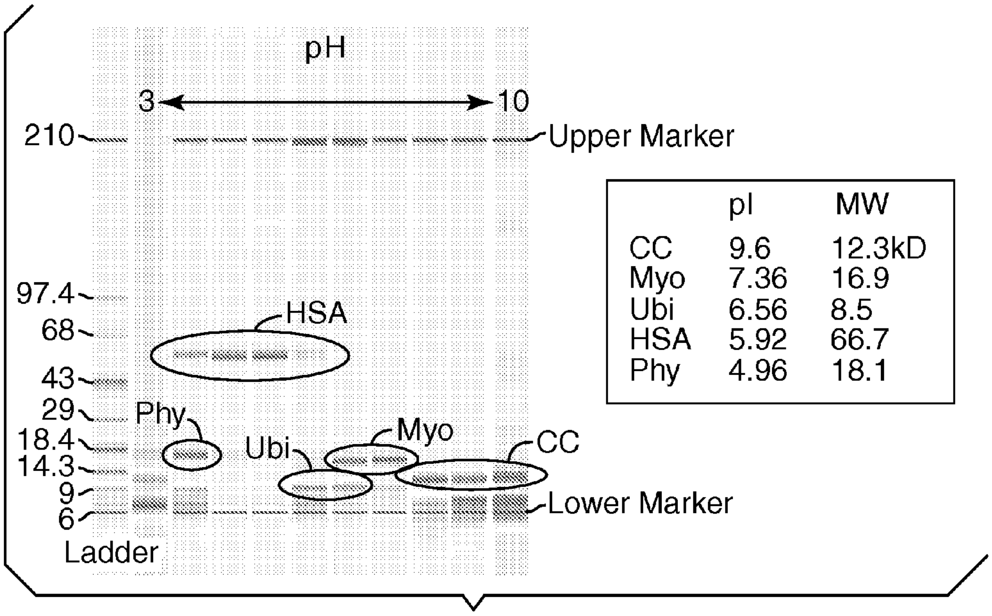
FIG. 22 is a two-dimensional virtual gel from protein fractions obtained from iso-electric focusing bins of a device of the invention that were analyzed on an Agilent 2100 Bioanalyzer.

Electropherograms were collected for each protein fraction and are presented FIG. 22 as a two-dimensional virtual gel. The first lane represents the standard protein ladder used to calibrate the subsequent electropherograms and the following lanes represent the protein fractions, increasing in pH. The theoretical protein pI and $M_w$, which were used to assign the proteins are given in Table 4 below.

TABLE 4

| | pI | $M_w$ (kD) |
|---|---|---|
| Cytochrome C | 9.6 | 12.3 |
| Myoglobin | 7.36 | 16.9 |
| Ubiquitin | 6.56 | 8.5 |
| Human Serum Albumin | 5.92 | 66.7 |
| Phyocyanin | 4.96 | 18.1 |

Figure 23A:
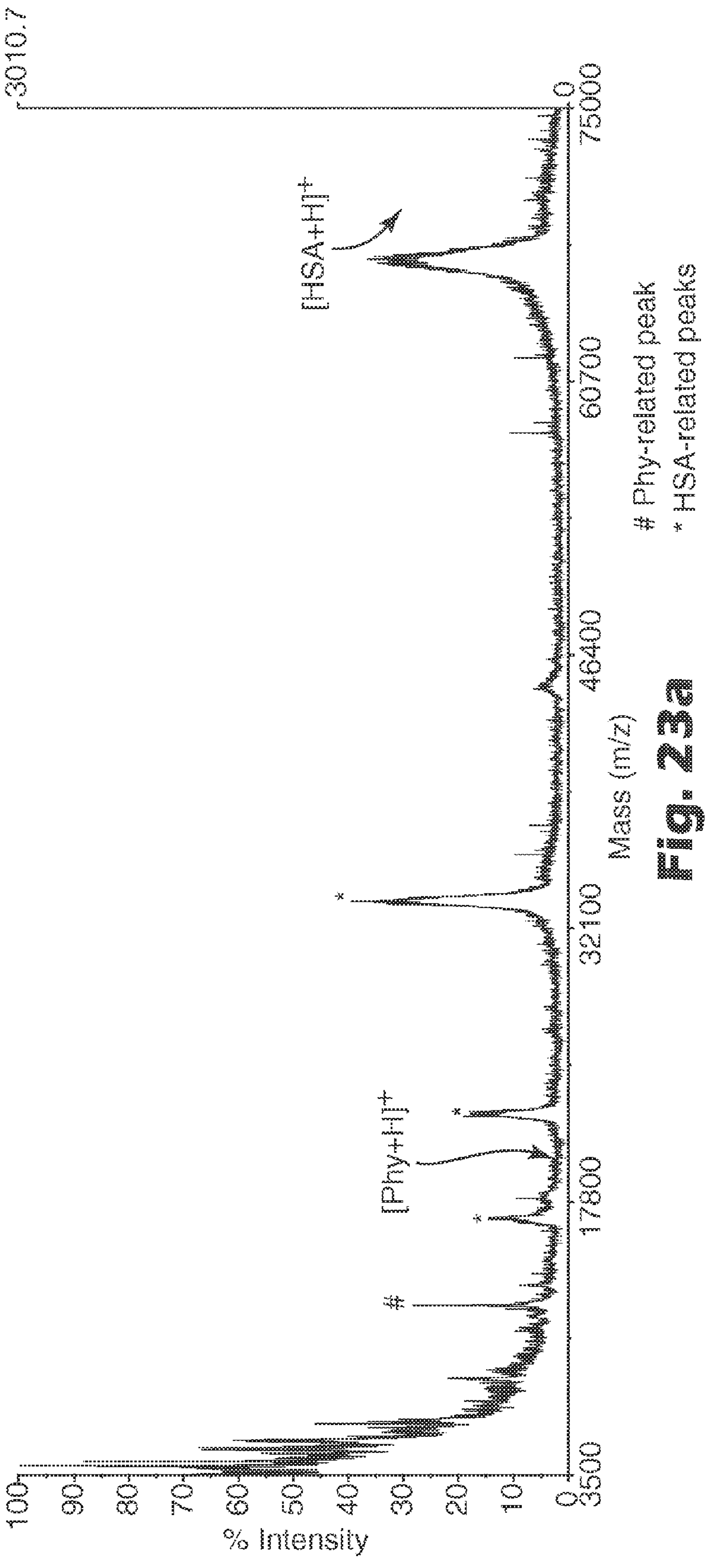
FIGS. 23*a, b, c*, and *d* are matrix assisted laser desorption ionization (MALDI) mass spectra of iso-electric focusing separated protein fractions.
Figure 23B:
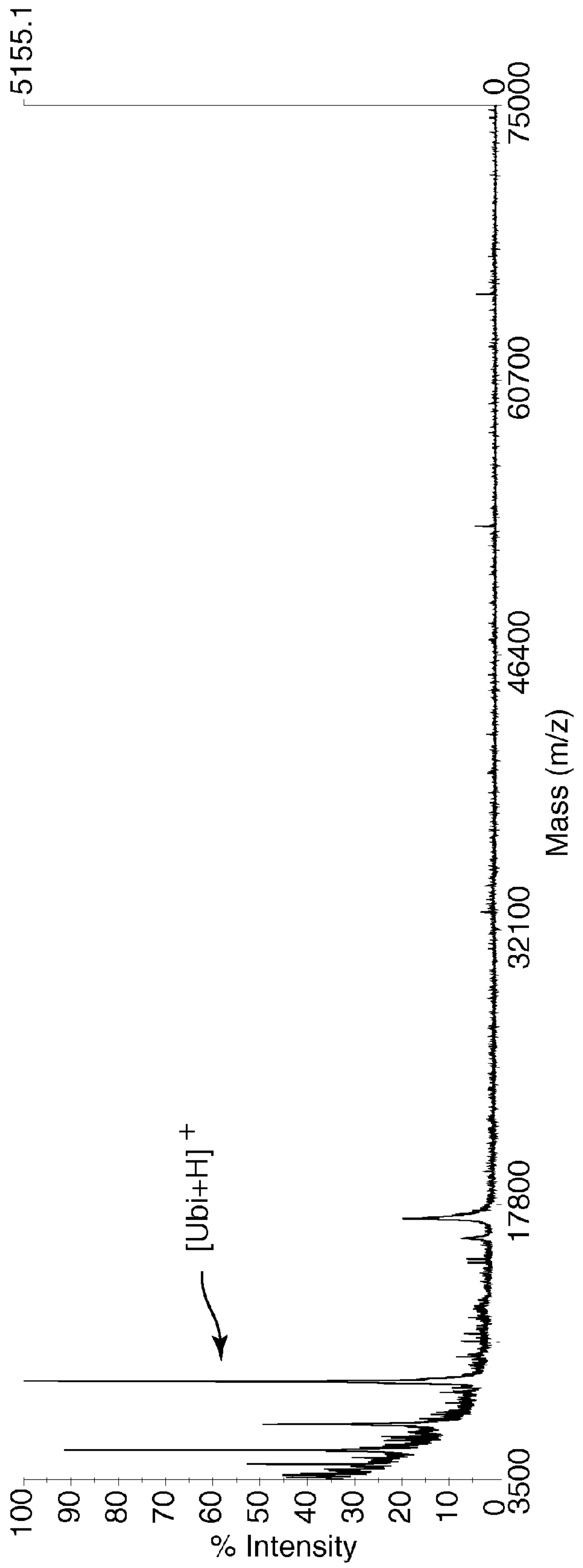
Figure 23C:
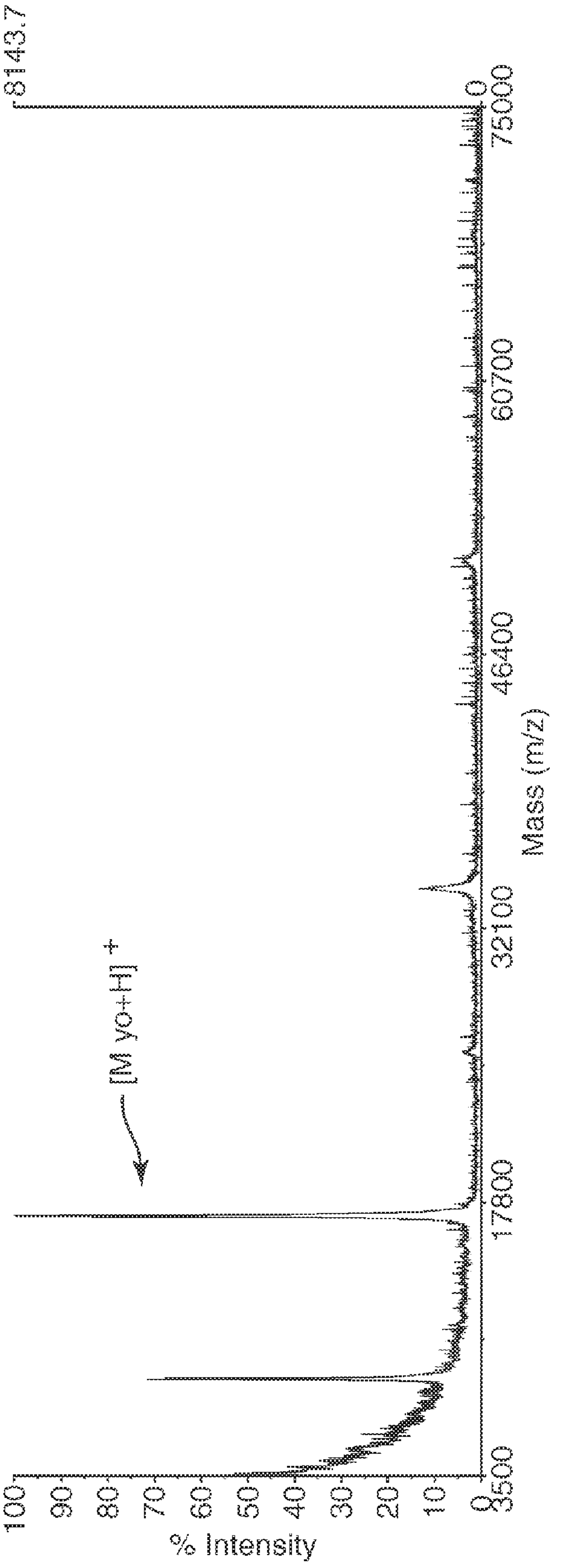
Figure 23D:
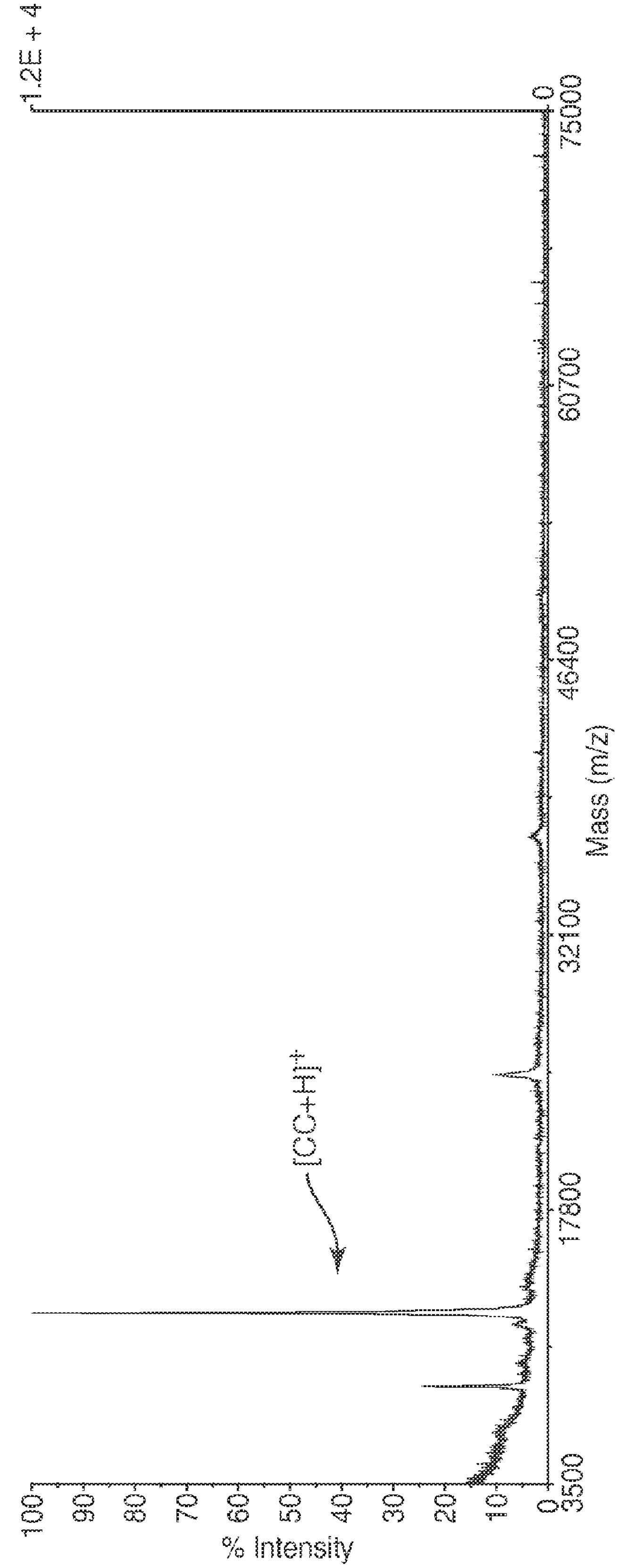
Figure 24A:
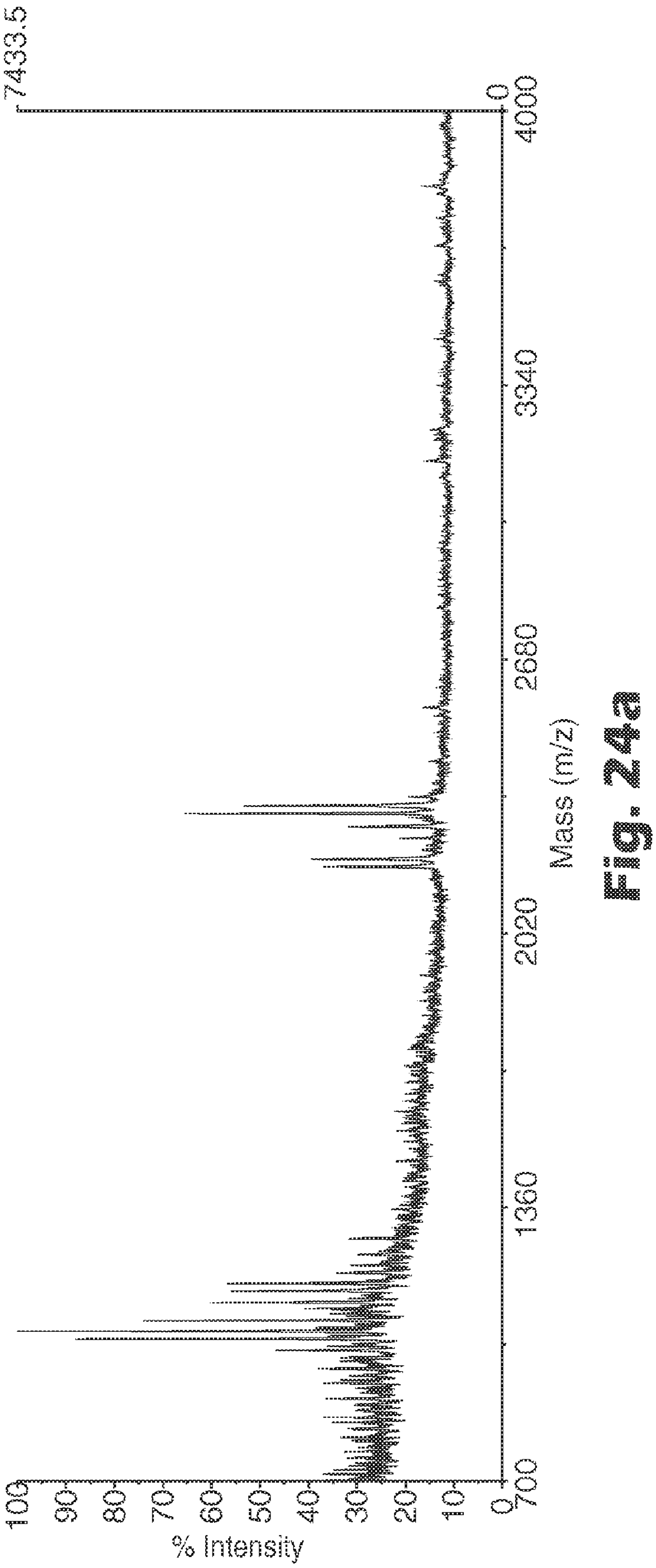
FIGS. 24*a, b*, and *c* are examples of MALDI peptide fingerprinting (m/z 700-4,000) of the iso-electric focused fractions from some of FIGS. 23*a, b, c*, and *d*.
Figure 24B:
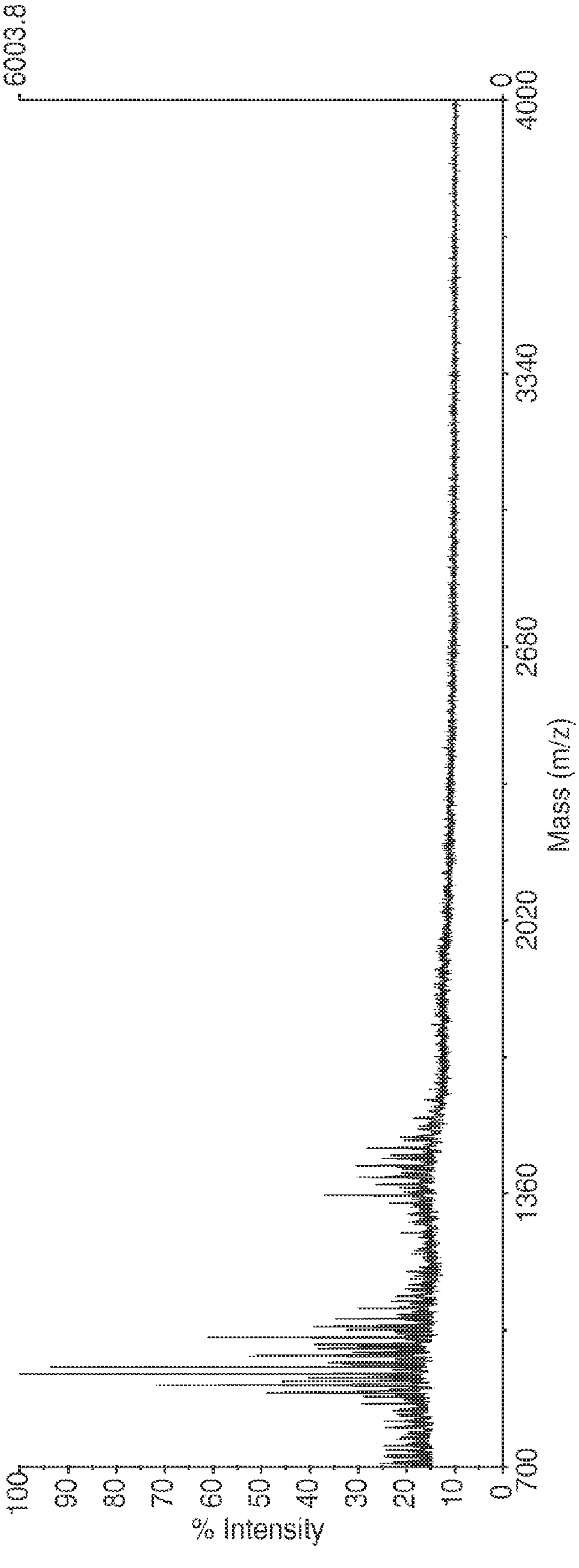
Figure 24C:
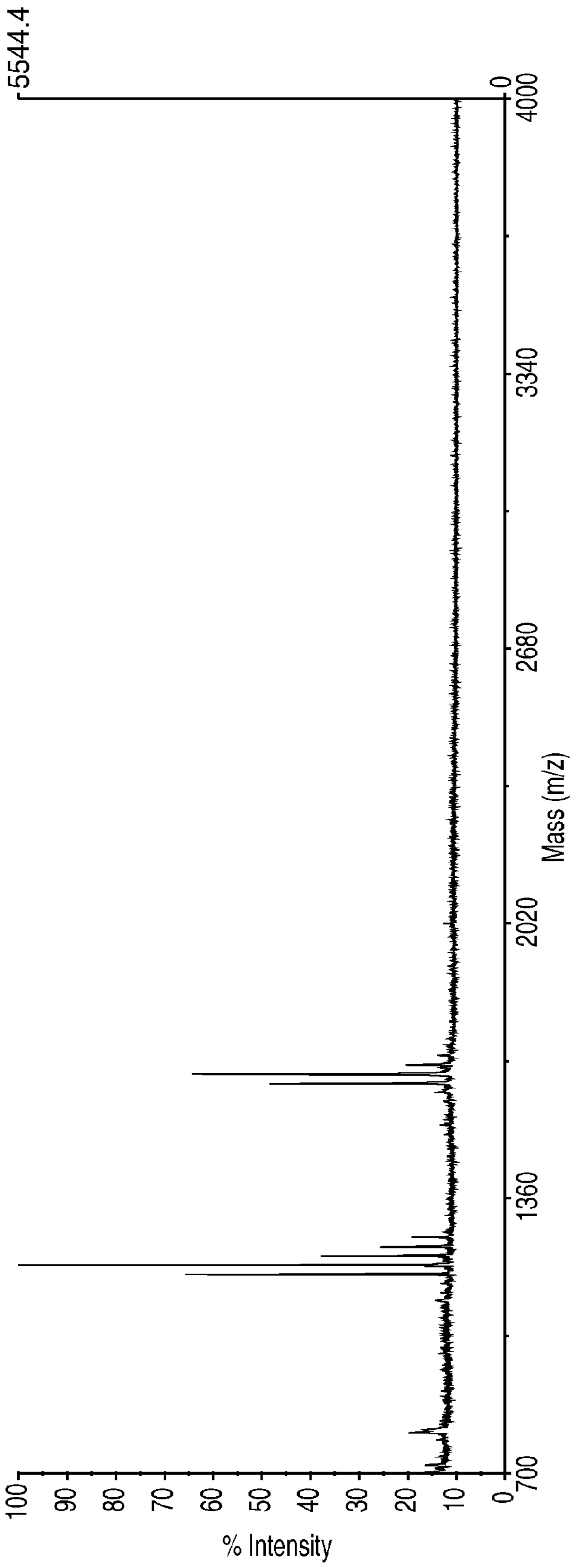

The separated protein fractions were subjected to matrix-assisted laser desorption ionization (MALDI) mass spectrometry. The spectra can be seen in FIGS. 23*a-d*. FIG. 23*a* shows the peaks for phycocyanin and HSA in F1 (Fraction 1), 23*b* shows ubiquitin in F4, 23*c* shows myoglobin in F6, and 23*d* is cytochrome C in F10. To further ascertain the identity of these proteins, proteolysis with trypsin was performed. FIG. 24 shows MALDI peptide fingerprinting (m/z 700-4,000) of IEF fractions in FIG. 23. The protein-database search results (Protein Prospector, UCSF Mass Spec Facility, http://prospector.ucsf.edu) confirmed that F1 contained HSA, F6 myoglobin, and F10 Cytochrome. However the search results did not detect phycocyanin peptides in F1 digest while the results from F4 did not provide a conclusive match for ubiquitin.

Example 4

Device in Accordance with the Invention and Use Thereof for IEF, Denaturing, Labeling and Capillary Electrophoresis-Off Device The substrate would be fabricated from polypropylene and sealed on both the first major surface and the second major surface with a cover film made of polyolefin with a pressure sensitive adhesive. An aluminum ring would be placed on the device below the denaturing bins. The polypropylene would be carbon loaded to function as the valving systems. The device would be fabricated by micro machining.

The unvented channel for IEF would be approximately 100 mm in arc length, and have 95 connected compartments. The angles of the leading and trailing edges of the connected compartments would be about 60°. The volume of the connected compartments would be approximately 0.75 μl. An additional compartment would be used to store the protein ladder that could also be separated by capillary electrophoresis on the disk. The protein ladder solution can contain denaturing chemistry.

A protein sample would be solubilized in a 10-50% glycerol/$H_2O$ solution with approximately 3% Bio-Rad Ampholytes (Catalog #163-1113). The final protein concentration should be about 5 mg/ml. The anolyte solution was a solution of $H_3PO_4$ at pH 2, and the catholyte solution was NaOH at pH 11.

The unvented channel would be filled with 100 μl of the protein-ampholyte solution. The channel would be filled in a manner that minimized bubble formation. The first sample well would be filled with the low pH anolyte solution, and the second sample well would be filled with the high pH catholyte solution.

The platinum electrodes would then be placed into the first and second sample wells, ensuring contact with the solution. A voltage of about 100 V/cm would be applied. The current and temperature arising from Joule heating would be monitored throughout. The current would likely decrease during the focusing of the protein sample and would be observed to reach a steady state value, which would indicate that focusing was complete.

The device would be placed on a rotating platform that controlled the position and speed of rotation of the device. The device would be spun at 5,000 rpm for 10 seconds with an acceleration of 100 rad.s$^{-2}$. The valves within the compartment connection structure would then be opened by a laser. The focused protein samples in the connected compartments would then be spun out into the chambers.

The chambers in this device would be pre-loaded with reagents for denaturing the proteins. The chambers contained β-mercaptoethanol or dithiothreitol to break the intra-protein sulfur linkages, an aqueous SDS solution to denature and solubilize the proteins and a fluorescent dye that derivatises the protein or associates with SDS micelles (NanoOrange, Molecular Probes, Eugene, Oreg.; Abs/Em: 470/570 nm). The chambers would also contain lower and upper marker proteins that could be used to scale the resultant electropherograms enabling direct sample comparison.

Once the valves within the compartment connection structure were opened, the solution would be heated to 95° C. for approximately 5 minutes using light ring technology described in WO 02/100347, the disclosure of which is incorporated by reference herein, to ensure complete denaturing of the protein sample. During the heating, the sample volume in the chambers would decrease in volume, which would serve to increase the protein concentration, thereby enhancing the detection of low concentration proteins. The chambers 244 also contained electrodes to measure the solution pH.

The valve within the chamber connection structure would then be opened with the IR laser. The device would then be rotated at 5,000 rpm for 10 seconds at an acceleration of about 100 rad.s$^{-2}$ to ensure fluid interconnect between the chamber and the capillary electrophoresis channel.

The electrophoresis capillaries would be prefilled with a poly(ethylene oxide)-Pluronic F-127 buffer solution. The poly(ethylene oxide) acts as separation matrix and surface coating to reduce non-specific binding of the protein to the capillary walls and electro-osmotic flow. The Pluronic surfactant enhances the surface hydrophilicity and provides an attractive surface for the poly(ethylene oxide) to dynamically coat onto. The running buffer is TrisHCl-SDS at pH 8.6.

The capillary electrophoresis capillary array would then be interfaced with the device.

The sample would be loaded into the capillary by electrokinetic injection to deliver a very thin sample plug. Laser-induced fluorescence (LIF) would be used as the detection mechanism by rotating the device to align the individual capillary channels with the LIF excitation-detection system.

Example 5

Device in Accordance with the Invention and Use Thereof for IEF, Denaturing, Labeling and Capillary Electrophoresis on Device A device in accordance with the invention, configured to perform IEF, sample preparation and capillary electrophoresis would be fabricated.

Figure 25:
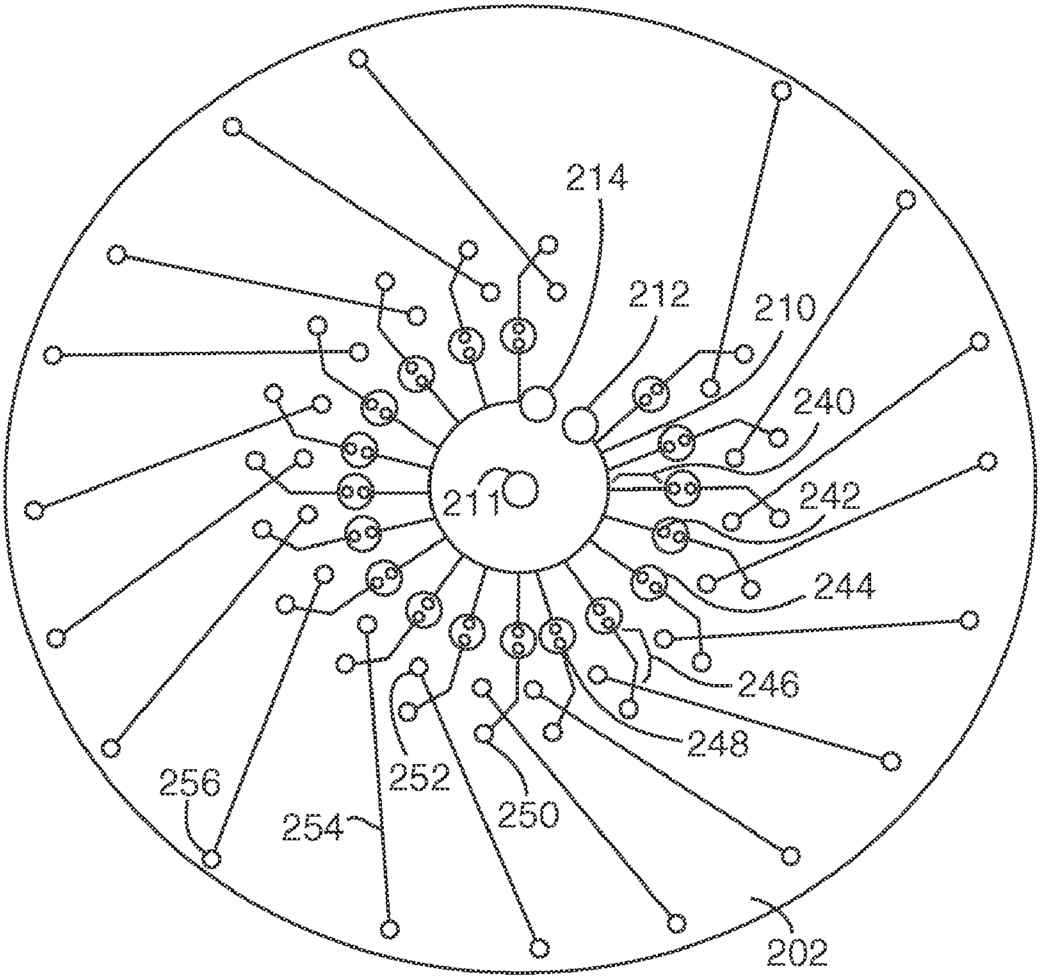
FIG. 25 is a plan view of a device in accordance with the invention configured for iso-electric focusing, denaturation, and capillary electrophoresis.

The substrate would be fabricated from polypropylene and sealed on both the first major surface and the second major surface with a cover film made of polyolefin with a pressure sensitive adhesive. An aluminum ring would be placed on the device below the denaturing bins. The polypropylene would be carbon loaded to function as the valving systems. The device would be fabricated by micro machining. The configuration of the device can be seen in FIG. 25. In FIG. 25, 211 represents the hub for rotation around a central axis, 210 represents the unvented channel configured for iso-electric focusing, 212 represents the firsts sample well, 214 represents the second sample well, 240 represents one of the plurality of compartment connection structures with 242 representing the valving system within a particular compartment connection structure, 244 represents one of the plurality of chambers that contains an electrode, 246 represents one of the plurality of chamber connection structures with 248 representing the valving system within a particular chamber connection structure, 250 represents an electrode, 254 represents an electrophoresis channel, and 252 and 256 represent the electrodes that are associated with particular electrophoresis channels.

The unvented channel for IEF would be approximately 100 mm in arc length, and have 95 connected compartments. The angles of the leading and trailing edges of the connected compartments would be about 60°. The volume of the connected compartments would be approximately 0.75 μl. An additional compartment would be used to store the protein ladder that could also be separated by capillary electrophoresis on the disk. The protein ladder solution can contain denaturing chemistry.

A protein sample would be solubilized in a 10-50% glycerol/$H_2O$ solution with approximately 3% Bio-Rad Ampholytes (Catalog #163-1113). The final protein concentration should be about 5 mg/ml. The anolyte solution was a solution of $H_3PO_4$ at pH 2, and the catholyte solution was NaOH at pH 11.

The unvented channel would be filled with 100 μl of the protein-ampholyte solution. The channel would be filled in a manner that minimized bubble formation. The first sample well would be filled with the low pH anolyte solution, and the second sample well would be filled with the high pH catholyte solution.

The platinum electrodes would then be placed into the first and second sample wells, ensuring contact with the solution. A voltage of about 100 V/cm would be applied. The current and temperature arising from Joule heating would be monitored throughout. The current would likely decrease during the focusing of the protein sample and would be observed to reach a steady state value, which would indicate that focusing was complete.

The device would be placed on a rotating platform that controlled the position and speed of rotation of the device. The device would be spun at 5,000 rpm for 10 seconds with an acceleration of 100 rad.s$^{-2}$. The valves within the compartment connection structure would then be opened by a laser. The focused protein samples in the connected compartments would then be spun out into the chambers.

The chambers in this device would be pre-loaded with reagents for denaturing the proteins. The chambers contained β-mercaptoethanol or dithiothreitol to break the intra-protein sulfur linkages, an aqueous SDS solution to denature and solubilize the proteins and a fluorescent dye that derivatises the protein or associates with SDS micelles (NanoOrange, Molecular Probes, Eugene, Oreg.; Abs/Em: 470/570 nm. The chambers would also contain lower and upper marker proteins that could be used to scale the resultant electropherograms enabling direct sample comparison.

Once the valves within the compartment connection structure were opened, the solution would be heated to 95° C. for approximately 5 minutes using light ring technology described in WO 02/100347, the disclosure of which is incorporated by reference herein, to ensure complete denaturing of the protein sample. During the heating, the sample volume in the chambers would decrease in volume, which would serve to increase the protein concentration, thereby enhancing the detection of low concentration proteins. The chambers 244 also contained electrodes to measure the solution pH.

The valve within the chamber connection structure would then be opened with the IR laser. The device would then be rotated at 5,000 rpm for 10 seconds at an acceleration of about 100 rad.s$^{-2}$ to ensure fluid interconnect between the chamber and the capillary electrophoresis channel.

The electrophoresis channels would be prefilled with an electrophoresis separation buffer, for example poly(ethylene oxide)-Pluronic F-127 buffer solution. The poly(ethylene oxide) acts as a separation matrix and surface coating to reduce non-specific binding of the protein to the capillary walls and electro-osmotic flow. The Pluronic surfactant enhances the surface hydrophilicity and provides an attractive surface for the poly(ethylene oxide) to dynamically coat onto. The running buffer is TrisHCl-SDS at pH 8.6.

The capillary electrophoresis channel would be approximately 50 μm in width and depth, and 70 mm in length.

The sample would be prevented from entering the capillary electrophoresis channel by a sieving matrix, 1% wt solution of polyethylene oxide (Mw 100,000). The sample would then be loaded into the capillary channel by electrokinetic cross-injection to deliver a highly concentrated, but very thin sample plug. This ensured high resolution over shorter separation lengths. Laser-induced fluorescence (LIF) would be used as the detection mechanism by rotating the device to align the individual capillary channels with the LIF excitation-detection device.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A device for processing sample material, the device comprising:

a substrate comprising first and second major surfaces and a hub defining a central axis of rotation for the substrate;

an unvented channel having an inner radius and outer radius, said channel adapted to fractionate a sample material; and at least one compartment connection structure in contact with said outer radius of said unvented channel.

2. The device of claim 1, wherein said substrate comprises a polymer.

3. The device of claim 1, wherein said substrate comprises polyolefins, polypropylene, polycarbonates, high-density polyethylene, polymethyl methacrylates, polystyrene, Teflon®, polysiloxanes, or a combination thereof.

4. The device of claim 1, wherein said substrate is about 0.1 mm to about 100 mm thick.

5. The device of claim 1, wherein said substrate is circular in shape and has a diameter of about 50 mm to about 500 mm.

6. The device of claim 1, wherein said unvented channel comprises a plurality of connected compartments.

7. The device of claim 6, wherein each of said plurality of connected compartments has a volume of about 100 microliter.

8. The device of claim 1, wherein said unvented channel is arc shaped.

9. The device of claim 8, wherein said unvented channel has an arc length of about 180 degrees or more.

10. The device of claim 1, further comprising at least one integrated electrode.

11. The device of claim 10, wherein said at least one integrated electrode is in connection with said unvented channel.

12. The device of claim 11, wherein said integrated electrode comprises a first piece in connection with said substrate and a second piece that is releasably attached to said first piece.

13. The device of claim 10, wherein said integrated electrode comprises a metallic film.

14. The device of claim 13, wherein said metallic film comprises platinum.

15. The device of claim 1, further comprising at least one cover film.

16. The device of claim 1, further comprising a plurality of compartment connection structures in contact with said outer radius of said unvented channel.

17. The device of claim 16, further comprising a plurality of chambers, each chamber defining a volume for containing sample material.

18. The device of claim 17, wherein said plurality of chambers contain reagents.

19. The device of claim 17, wherein said plurality of chambers are connected to said plurality of compartment connection structures.

20. The device of claim 19, further comprising at least one chamber valve.

21. The device of claim 20, wherein said chamber valve functions through laser ablation of at least a portion of said chamber valve.

22. The device of claim 19, further comprising a plurality of electrophoresis channels, wherein the plurality of electrophoresis channels extend generally radially outward relative to the axis of rotation of the substrate.

23. The device of claim 22, further comprising a plurality of chamber connection structures located between at least one chamber and at least one electrophoresis channel, and at least one chamber valve.

24. The device of claim 23, wherein said substrate comprises a material that absorbs laser energy.

25. The device of claim 24, wherein said material that absorbs energy comprises carbon-loaded polymer.

26. The device of claim 24, wherein said chamber valve functions through laser ablation of at least a portion of said chamber valve.

27. A method of fractionating an analyte sample, said method comprising the steps of:

loading said sample into a device of claim 24, and rotating said device to cause said sample to fractionate.

28. The device of claim 23, further comprising a plurality of sample preparation chambers, each sample preparation chamber defining a volume for containing sample material.

29. The device of claim 28, further comprising a preparation connection structure located between the at least one electrophoresis channel and at least one sample preparation chamber, and a valve structure.

30. The device of claim 28, wherein the plurality of sample preparation chambers contain reagents for protein digestion.

31. The device of claim 28, wherein the plurality of sample preparation chambers are configured to be heated.

32. The device of claim 1, wherein the wetability of the surface of said unvented channel is different from that of the bulk of the substrate material coated with a compound that improves the wetability of the unvented channel.

33. The device of claim 1, wherein the surface of said unvented channel has been surface modified to create an immobilized pH gradient.

34. The device of claim 1, wherein the distance between said central axis and said outer radius oscillates.

35. The device of claim 1, wherein the distance between said central axis and said inner radius oscillates.

36. A method of performing iso-electric focusing of a sample containing analytes, said method comprising the steps of:

(a.) loading a sample onto a device, the device comprising a substrate having first and second major surfaces and a hub defining a central axis of rotation for the substrate; an unvented channel having an inner radius and outer radius and first and second sample wells; and a plurality of compartment connection structures, wherein said compartment connection structures are in contact with said outer radius of said unvented channel, wherein the sample is loaded into the first or second sample well;

(b.) allowing the sample to enter the unvented channel of the device;

(c.) adding anolyte solution to the first sample well of the device;

(d.) adding catholyte solution to the second sample well of the device;

(e.) contacting electrodes with the solutions in the sample wells;

(f.) applying a voltage to the electrodes; and (g.) rotating the device to cause the solutions to move from the unvented channel to the plurality of compartment connection structures.

37. The method of claim 36, wherein valves in the plurality of compartment connection structures are opened before the device is rotated.

38. The method of claim 36, wherein said solutions move through the plurality of compartment connection structures to a plurality of chambers.

39. The method of claim 36, wherein said chambers contain chemical reagents.

40. The method of claim 36, wherein said chambers containing the solutions and the reagents are heated.

41. A method of processing a solution containing analytes, said method comprising the steps of:

(a.) loading the solution into a device, said device comprising (i) a substrate having first and second major surfaces and a hub defining a central axis of rotation for the substrate, and (ii) an unvented channel within said substrate;

(b.) allowing the solution to enter the unvented channel;

(c.) separating the analytes of the solution; and (d.) applying a centrifugal force to the solution, thereby fractionating said solution.

42. The method of claim 41, wherein said analytes are separate by isoelectric focusing.

* * * * *

UNITED STATES PATENT AND TRADEMARK OFFICE

CERTIFICATE OF CORRECTION

PATENT NO. : 7,238,269 B2 Page 1 of 1
APPLICATION NO. : 10/610949
DATED : July 3, 2007
INVENTOR(S) : Samuel J. Gason It is certified that error appears in the above-identified patent and that said Letters Patent is hereby corrected as shown below:

On Page 2, in Column 2, under (Other Publications)
Line 3, delete “Diagnostic” and insert -- Diagnostics --, therefor.
Line 5, delete “[retrived” and insert -- [retrieved --, therefor.
Line 10, delete “(Nov.” and insert -- (Nov., --, therefor.

Column 4
Line 12, delete “an” and insert -- can --, therefor.
Lines 41-42, delete “displacment” and insert -- displacement --, therefor.
Line 45, after “system” insert -- . --.

Column 9
Line 41, delete “acryloxypropyltrimeth–oxysilane” and insert -- acryloxypropyltrimethoxysilane --, therefor.

Column 26
Line 48, delete “amylogulcosidase” and insert -- amyloglucosidase --, therefor.

Column 27
Line 17, delete “phyocyanin)” and insert -- phycocyanin) --, therefor.

Column 28
Line 22, delete “Phyocyanin” and insert -- Phycocyanin --, therefor.

Signed and Sealed this

Sixth Day of May, 2008

JON W. DUDAS
*Director of the United States Patent and Trademark Office*